(12) United States Patent
Kato et al.

(10) Patent No.: US 9,234,897 B2
(45) Date of Patent: Jan. 12, 2016

(54) METHOD FOR DISTINGUISHING MESENCHYMAL STEM CELL USING MOLECULAR MARKER AND USE THEREOF

(75) Inventors: Yukio Kato, Hiroshima (JP); Takeshi Kawamoto, Hiroshima (JP); Koichiro Tsuji, Hiroshima (JP); Akira Igarashi, Hiroshima (JP); Masakazu Shimizu, Kyoto (JP)

(73) Assignee: TWO CELLS CO., LTD, Hiroshima (JP)

( * ) Notice: Subject to any disclaimer, the term of this patent is extended or adjusted under 35 U.S.C. 154(b) by 1661 days.

(21) Appl. No.: 11/887,362

(22) PCT Filed: Mar. 30, 2006

(86) PCT No.: PCT/JP2006/306658
§ 371 (c)(1),
(2), (4) Date: Sep. 28, 2007

(87) PCT Pub. No.: WO2006/106823
PCT Pub. Date: Oct. 12, 2006

(65) Prior Publication Data
US 2009/0232773 A1 Sep. 17, 2009

(30) Foreign Application Priority Data
Mar. 31, 2005 (JP) ................. 2005-104563

(51) Int. Cl.
*C12N 5/00* (2006.01)
*G01N 33/68* (2006.01)
*C12Q 1/68* (2006.01)
*G01N 33/569* (2006.01)

(52) U.S. Cl.
CPC .......... *G01N 33/6845* (2013.01); *C12Q 1/6881* (2013.01); *G01N 33/56966* (2013.01); *C12Q 2600/158* (2013.01)

(58) Field of Classification Search
CPC .......................... C12N 5/0663; C12N 5/0667
See application file for complete search history.

(56) References Cited

U.S. PATENT DOCUMENTS

| | | | | |
|---|---|---|---|---|
| 5,147,783 A * | 9/1992 | Uda et al. | ...... | 435/7.23 |
| 5,338,547 A * | 8/1994 | Kennedy et al. | ...... | 424/757 |
| 5,486,359 A * | 1/1996 | Caplan et al. | ...... | 424/93.7 |
| 6,521,407 B1 * | 2/2003 | Warenius et al. | ...... | 435/6.14 |
| 6,890,720 B1 | 5/2005 | Serre et al. | | |
| 7,364,863 B2 | 4/2008 | Buhring et al. | | |
| 2002/0068046 A1 * | 6/2002 | Dai et al. | ...... | 424/93.7 |
| 2002/0142457 A1 * | 10/2002 | Umezawa et al. | ...... | 435/366 |
| 2003/0161817 A1 | 8/2003 | Young et al. | | |
| 2003/0215420 A1 * | 11/2003 | D'Armiento et al. | ...... | 424/85.1 |
| 2005/0214873 A1 | 9/2005 | Buehring et al. | | |
| 2006/0019256 A1 * | 1/2006 | Clarke et al. | ...... | 435/6 |
| 2006/0078993 A1 * | 4/2006 | Phan et al. | ...... | 435/366 |
| 2006/0166214 A1 | 7/2006 | Kato et al. | | |
| 2011/0274667 A1 * | 11/2011 | Donofrio et al. | ...... | 424/93.7 |

FOREIGN PATENT DOCUMENTS

| | | |
|---|---|---|
| EP | 1 475 438 | 11/2004 |
| EP | 1605044 | 12/2005 |
| JP | 2003-052360 | 2/2003 |
| JP | 2003-052365 | 2/2003 |
| JP | 2004-290189 | 10/2004 |
| JP | 2005-027579 | 2/2005 |
| WO | WO 02/46373 | 6/2002 |
| WO | WO 03/016916 | 2/2003 |
| WO | WO 03/106492 | 12/2003 |
| WO | WO 2004/025293 | 3/2004 |
| WO | WO 2004/044142 | 5/2004 |

OTHER PUBLICATIONS

Pontikoglou C et al. 2008, Human bone marrow native mesenchymal stem cells. Regen Med 3: 731-41.*
Lee et al. 2001. A comparative study of gene expression in murine embryos developed in vivo, cultured in vitro, and cocultured with human oviductal cells using messenger ribonucleic acid differential display. Biol. Reprod. 64: 910-17.*
Kern S et al. 2006. Comparative analysis of mesenchymal stem cells from bone marrow, umbilical cord blood, or adipose tissue. Stem Cells 24:1294-1301.*
Meirelles L et al. 2006. Mesenchymal stem cells reside in nearly all post-natal organs and tissues. J Cell Sci 119: 2204-2213.*
Doi M et al. 2002. Genome-wide Screening by cDNA Microarray of Genes Associated with Matrix Mineralization by Human Mesenchymal Stem Cells in Vitro. Biochem Biophys Res Comm 290: 381-390.*
Wagner W et al. 2005. Comparative characteristics of mesenchymal stem cells from human bone marrow, adipose tissue, and umbilical cord blood. Exp Hematol 33: 1402-1416.*
Maitra R et al. 2003. Cloning, molecular characterization, and expression analysis of Copine 8. Biochem Biophys Res Comm 303: 842-847.*
European Search Report mailed Dec. 17, 2009 in corresponding European Application No. 06730606.8.

(Continued)

*Primary Examiner* — Lora E Barnhart Driscoll
(74) *Attorney, Agent, or Firm* — Leanne Rakers

(57) ABSTRACT

Disclosed is a method for distinguishing a mesenchymal stem cell comprising, using at least one gene selected from the genes having the nucleotide sequences indicated by the accession numbers shown in Table 1 as a distinguish marker, detecting the difference in expression of the distinguish marker between a mesenchymal stem cell and a connective tissue cell to distinguish the mesenchymal stem cell from the connective tissue cell. This method enables to distinguish an undifferentiated mesenchymal stem cell from other connective tissue cell such as fibroblasts, osteoblasts, chondrocytes and adipose cells with good accuracy. A mesenchymal stem cell given by this method or a composition comprising the mesenchymal stem sell can be used as a therapeutic for use in the regenerative medicine.

7 Claims, 2 Drawing Sheets

(56) References Cited

OTHER PUBLICATIONS

Deschaseaux et al., "Direct selection of human bone marrow mesenchymal stem cells using an anti-CD49a antibody reveals their $CD45^{med,low}$ phenotype", British Journal of Haematology, vol. 122, pp. 506-517 (2003).

Botuyan et al., "Structural Basis of BACH1 Phosphopeptide Recognition by BRCA1 Tandem BRCT Domains", Structure, vol. 12, pp. 1137-1146 (Jul. 2004).

Affymetrix Product Catalog, Jul. 1, 2002, p. 1, XP002267612: Product: Human Genome U133A Array; Array Finder.

Ishii et al., "Molecular markers distinguish bone marrow mesenchymal stem cells from fibroblasts", Biochemical and Biophysical Research Communications, vol. 332, pp. 297-303 (2005).

Seguchi, T. et al.: "Decreased Expression of Filaggrin in Atopic Skin," Archives of Cermatological Research, Springer, International Berlin, DE, vol. 288, Jan. 1, 1996, pp. 442-446.

European Search Report dated Feb. 11, 2011, issued in corresponding European Application No./Patent No. 10013575.5-1222/2270226.

Connor J.R. et al. "Human cartilage glycoprotein 39 (HC gp-39) mRNA expression in adult and fetal chondrocytes, osteoblasts and osteocytes by in-situ hybridization." Osteoarthritis and Cartilage vol. 8, pp. 87-95, 2000.

Shih-Chieh Hung et al. "Gene expression profiles of early adipogenesis in human mesenchymal stem cells". Gene 340, pp. 141-150. 2004.

Xinping Zhang et al. "Primary murine limb bud mesenchymal cells in long-term culture complete chondrocyte differentiation: TGF-β delays hypertrophy and PGE 2 inhibits terminal differentiation" Bone 34, pp. 809-817. 2004.

Uddin, M., et al. (2004), "Sister grouping of chimpanzees and humans as revealed by genome-wide phylogenetic analysis of brain gene expression profiles", *PNAS*, 101(9): 2957-2962.

* cited by examiner

METHOD FOR DISTINGUISHING MESENCHYMAL STEM CELL USING MOLECULAR MARKER AND USE THEREOF

TECHNICAL FIELD

The present invention relates to a method for detecting, distinguishing, and separating mesenchymal stem cells, especially, to a method for distinguishing mesenchymal stem cells from connective tissue cells such as fibroblasts, osteoblasts, chondrocytes, adipose cells, etc. by using a gene marker, a protein marker, and/or the like marker for detecting mesenchymal stem cells, the markers being expressed in a different way in mesenchymal stem cells and in the other connective tissue cells.

BACKGROUND ART

Mesenchymal stem cells are present in mammalian marrows etc. and known as pluripotential stem cells, which can differentiate into adipose cells, cartilage cells, and bone cells. Due to its pluripotency, mesenchymal stem cells are highly expected as transplantation material for use in regenerative medicine for many kinds of tissues. That is, the use of mesenchymal stem cell enables "regenerative medicine by cell transplantation" for regenerating lost tissues lost due to diseases or impairment and have not been able to be regenerated by a conventional remedy method. More specifically, therapeutic treatments have been started or planed, which are for example, transplantation of marrow mesenchymal stem cells to a patient of lower limb ischemia (Buerger's disease), transplantation of marrow mesenchymal stem cells to a patient of a periodontal disease, transplantation of marrow mesenchymal stem cells to a patient of osteoarthritis, transportation of amniotic epithelium sheet to burn injured portion, transportation of amniotic stem cells to a patient of diabetes mellitus, and the other transplantation.

In order to use mesenchymal stem cells for regenerative medicine, the stem cells should be collected from a living tissue and then multiplied without differentiation, and the multiplied and undifferentiated stem cells should be induced to differentiate to desired cells in order to prepare tissue for the regenerative medicine.

The inventors of the present invention have reported a method of easily collecting mesenchymal stem cells by separating mesenchymal stem cells from an oral cavity tissue, which method is safe for an individual from which the mesenchymal stem cells are collected (see Patent Citation 1). Moreover, the inventors of the present invention have reported a culturing method, which can give a significantly larger amount of mesenchymal stem cells than can a conventional culturing method. The culturing method having been reported by the inventors of the present invention is based on a fact found by the inventors that mesenchymal stem cells can be multiplied at a dramatically fast rate by culturing the mesenchymal stem cells in the presence of an extracellular matrix of a basement membrane or in a medium containing fibroblast growth factor (FGF) etc. and this culturing method can multiply mesenchymal stem cells without the differentiating ability thereof (see Patent Citation 2).

These arts are not enough to make the regenerative medicine using the mesenchymal stem cells practically applicable. To speak specifically, for the preparation of the tissue for regenerative medicine by inducing the differentiation of the cultured and multiplied mesenchymal stem cells to desired cells, the cultured cells should be confirmed beforehand that they are mesenchymal stem cells. That is, it is necessary to develop a method of detecting and distinguishing the mesenchymal stem cells after the culturing and multiplication.

To solve this technical problem, the inventors of the present invention have developed a method of effectively identifying and separating mesenchymal stem cells and fibroblast, which are morphologically similar and thus difficult to be distinguish, the method using a gene maker and/or a protein marker for detecting mesenchymal stem cells (see Patent Citation 3).

[Patent Citation 1]
Japanese Patent Application Publication, Tokukai, No. 2003-52365 (published on Feb. 25, 2003).
[Patent Citation 2]
Japanese Patent Application Publication, Tokukai, No. 2003-52360 (published on Feb. 25, 2003).
[Patent Citation 3]
Japanese Patent Application Publication, Tokukai, No. 2005-27579 (published on Feb. 3, 2005).

DISCLOSURE OF INVENTION

Technical Problems

As described above, mesenchymal stem cells, which differentiate to bones, cartilages, fats, muscles, tendons/ligaments, nerves, etc., have been highly expected to be applicable to the regenerative medicine as cells for transplantation to remedy impairment of these tissues. Conventionally, the confirmation of the mesenchymal stem cells can be carried out in vitro or by providing the differentiation ability thereof in vivo. The practical use of the tissue regenerative medicine of the mesenchymal stem cells cannot be attained without exact, accurate, and easy method to confirm that the cells are mesenchymal stem cells and the mesenchymal stem cells keep its pluripotency.

It is true that the method disclosed in Patent Citation 3 is sufficient to identify and distinguish the mesenchymal stem cells and fibroblast. However, bone marrows etc. contain many other connective tissue cells other than fibroblasts, such as osteoblasts, chondrocytes, adipose cells, etc.

Therefore, the art to distinguish the mesenchymal stem cells from fibroblast is not enough to realize practical regenerative medicine using the mesenchymal stem cells. Accordingly, there have been a high demand to develop an art to distinguish and separate the undifferentiated mesenchymal stem cells from the other connective tissue cells such as fibroblasts, osteoblasts, chondrocytes, adipose cells, etc. with exactness, accuracy, and easiness. The development of the art will be beneficial for the regenerative medicine because the art can distinguish the mesenchymal stem cells that keep the pluripotency thereof, from the undifferentiated mesenchymal stem cells mass-produced.

The present invention was accomplished in view of the aforementioned problem. An object of the present invention is to provide a method of exactly and accurately distinguishing and/or separating mesenchymal stem cells from the connective tissue cells such as fibroblasts, osteoblasts, chondrocytes, adipose cells, etc., and use of the same method.

Technical Solution

The inventors of the present invention diligently worked to attain the object. The inventors studied expression profiles of genes in mesenchymal stem cells and connective tissue cells such as fibroblasts and others. As a result, the inventors newly found that there are genes whose expression is specific to mesenchymal stem cells but whose expressions in the connective tissue cells such as fibroblast and others are clearly different from the expression in mesenchymal stem cells. Based on this novel finding, the present invention was accomplished. The present invention, based on this novel finding, encompass the following inventions.

(1) A method of distinguishing mesenchymal stem cells, including:

distinguishing the mesenchymal stem cells from connective tissue cells by detecting a difference between expression in the mesenchymal stem cells and expression in the connective tissue cells by using a distinguishing marker(s), the distinguishing marker(s) being at least one of genes having the base sequences identified with accession numbers listed in Table 1a to 1j.

TABLE 1a

| Classification 1 | Gene symbol | Gene title | Genbank number |
| --- | --- | --- | --- |
| ATP/GTP binding-1 | BRIP1 | BRCA1 interacting protein C-terminal helicase 1 | NM_032043 |
| ATP/GTP binding-2 | PASK | PAS domain containing serine/threonine kinase | NM_015148 |
| ATP/GTP binding-3 | RAC2 | ras-related C3 botulinum toxin substrate 2 (rho family, small GTP binding protein Rac2) | NM_002872 |
| ATP/GTP binding-4 | KIF18A | kinesin family member 18A | NM_031217 |
| ATP/GTP binding-5 | NEK7 | NIMA (never in mitosis gene a)-related kinase 7 | NM_133494 |
| ATP/GTP binding-6 | ARL4C | ADP-ribosylation factor-like 4C | NM_005737 |
| ATP/GTP binding-7 | EDEM1 | ER degradation enhancer, mannosidase alpha-like 1 | NM_014674 |
| ATP/GTP binding-8 | CAMK2D | calcium/calmodulin-dependent protein kinase (CaM kinase) II delta | NM_172127 |

TABLE 1b

| Classification 3 | Gene symbol | Gene title | Genbank number |
| --- | --- | --- | --- |
| cell growth and/or maintenance-1 | CCND1 | cyclin D1 (PRAD1: parathyroid adenomatosis 1) | NM_053056 |
| cell growth and/or maintenance-2 | CDC25A | cell division cycle 25A | NM_001789 |
| cell growth and/or maintenance-3 | IER3 | immediate early response 3 | NM_052815 |
| cell growth and/or maintenance-4 | BCL2 | B-cell CLL/lymphoma 2 | NM_000633 |
| cell growth and/or maintenance-5 | NALP1 | NACHT, leucine rich repeat and PYD containing 1 | NM_033004 |
| cell growth and/or maintenance-6 | PAK3 | p21 (CDKN1A)-activated kinase 3 | NM_002578 |
| cell growth and/or maintenance-7 | PODXL | podocalyxin-like | NM_001018111 |
| cell growth and/or maintenance-8 | CCL26 | chemokine (C-C motif) ligand 26 | NM_006072 |
| cell growth and/or maintenance-9 | FBLN1 | fibulin 1 | NM_006486 |
| cell growth and/or maintenance-10 | LAMA1 | laminin, alpha 1 | NM_005559 |
| cell growth and/or maintenance-11 | NTNG1 | netrin G1 | NM_014917 |

TABLE 1c

| | Gene symbol | Gene title | Genbank number |
| --- | --- | --- | --- |
| Classification 4 | | | |
| cytokine-1 | GDF15 | growth differentiation factor 15 | NM_004864 |
| cytokine-2 | IL6 | interleukin 6 (interferon, beta 2) | NM_000600 |
| cytokine-3 | CTGF | connective tissue growth factor | NM_001901 |

TABLE 1c-continued

|  | Gene symbol | Gene title | Genbank number |
|---|---|---|---|
| cytokine-4 | VEGF | vascular endothelial growth factor | NM_001025366 |
| cytokine-5 | VEGFC | vascular endothelial growth factor C | NM_005429 |
| cytokine-6 | HGF | hepatocyte growth factor (hepapoietin A; scatter | NM_000601 |
| Classification 5 | | | |
| cytoskeleton-1 | KRT19 | keratin 19 | NM_002276 |
| cytoskeleton-2 | KRTAP1-5 | keratin associated protein 1- | NM_031957 |
| cytoskeleton-3 | KRTAP2-1 | keratin associated protein 2- | BC012486 |
| cytoskeleton-4 | KRTHA4 | keratin, hair, acidic, 4 | NM_021013 |
| cytoskeleton-5 | CKAP2 | cytoskeleton associated protein 2 | NM_018204 |
| cytoskeleton-6 | KRTAP1-1 | keratin associated protein 1- | NM_030967 |
| cytoskeleton-7 | KRT18 | keratin 18 | NM_000224 |
| cytoskeleton-8 | KAP2.1B | keratin associated protein 2.1B | AJ406929 |
| cytoskeleton-9 | SSH1 | slingshot homolog 1 (*Drosophila*) | NM_018984 |
| Classification 6 | | | |
| enzyme-1 | LXN | latexin | NM_020169 |
| enzyme-2 | IFI30 | interferon, gamma-inducible protein 30 | NM_006332 |
| enzyme-3 | CPA4 | carboxypeptidase A4 | NM_016352 |

TABLE 1d

|  | Gene symbol | Gene title | Genbank number |
|---|---|---|---|
| Classification 7 | | | |
| extracellular matrix-1 | CHI3L1 | chitinase 3-like 1 (cartilage glycoprotein-39) | NM_001276 |
| extracellular matrix-2 | KRT23 | keratin 23 (histone deacetylase inducible) | NM_015515 |
| extracellular matrix-3 | FLG | filaggrin | NM_002016 |
| extracellular matrix-4 | ADAMTS1 | a disintegrin-like and metalloprotease (reprolysin type) with thrombospondin type 1 motif, 1 | NM_006988 |
| extracellular matrix-5 | FRMD5 | FERM domain containing 5 | NM_001031729 |
| Classification 8 | | | |
| growth factor or receptor-1 | IGFBP1 | insulin-like growth factor binding protein 1 | NM_000596 |
| growth factor or receptor-2 | CFI | complement factor I | NM_000204 |
| growth factor or receptor-3 | ESM1 | endothelial cell-specific molecule 1 | NM_007036 |
| growth factor or receptor-4 | F2RL1 | coagulation factor II (thrombin) receptor-like 1 | NM_005242 |
| growth factor or receptor-5 | MET | met proto-oncogene (hepatocyte growth factor receptor) | NM_000245 |
| growth factor or receptor-6 | HTR7 | 5-hydroxytryptamine (serotonin) receptor 7 (adenylate cyclase-coupled) | NM_000872 |
| growth factor or receptor-7 | IGFBP3 | insulin-like growth factor binding protein 3 | NM_001013398 |

TABLE 1e

|  | Gene symbol | Gene title | Genbank number |
|---|---|---|---|
| Classification 9 | | | |
| membrane-1 | ABHD2 | abhydrolase domain containing 2 | NM_007011 |
| membrane-2 | ITGA2 | integrin, alpha 2 (CD49B, alpha 2 subunit of VLA-2 receptor) | NM_002203 |

TABLE 1e-continued

| | Gene symbol | Gene title | Genbank number |
|---|---|---|---|
| membrane-3 | LAMA3 | laminin, alpha 3 | NM_198129 |
| membrane-4 | NETO2 | neuropilin (NRP) and tolloid (TLL)-like 2 | NM_018092 |
| membrane-5 | NTN4 | netrin 4 | NM_021229 |
| membrane-6 | PTGER1 | prostaglandin E receptor 1 (subtype EP1), 42 kDa | NM_000955 |
| membrane-7 | EPHB2 | EPH receptor B2 | NM_017449 |
| membrane-8 | SFRP1 | secreted frizzled-related protein 1 | NM_003012 |
| membrane-9 | CD33L3 | CD33 antigen-like 3 | NM_213602 |
| membrane-10 | GLIPR1 | GLI pathogenesis-related 1 (glioma) | NM_006851 |
| membrane-11 | UGCG | UDP-glucose ceramide glucosyltransferase | NM_003358 |
| membrane-12 | ADORA1 | adenosine A1 receptor | NM_000674 |
| Classification 10 | | | |
| membrane binding protein-1 | ANXA10 | annexin A10 | NM_007193 |
| membrane binding protein-2 | RARRES1 | retinoic acid receptor responder (tazarotene induced) 1 | NM_206963 |
| membrane binding protein-3 | HNT | neurotrimin | NM_016522 |
| membrane binding protein-4 | CNTNAP3 | contactin associated protein-like 3 | NM_033655 |

TABLE 1f

| Classification 11 | Gene symbol | Gene title | Genbank number |
|---|---|---|---|
| protein binding-1 | SYT1 | synaptotagmin I | NM_005639 |
| protein binding-2 | MLF1 | myeloid leukemia factor 1 | NM_022443 |
| protein binding-3 | CDCP1 | CUB domain-containing protein 1 | NM_022842 |
| protein binding-4 | KIAA0746 | KIAA0746 protein | NM_015187 |
| protein binding-5 | PSCDBP | pleckstrin homology, Sec7 and coiled-coil domains, binding protein | NM_004288 |
| protein binding-6 | SKI | v-ski sarcoma viral oncogene homolog (avian) | NM_003036 |
| protein binding-7 | SNX25 | sorting nexin 25 | NM_031953 |
| protein binding-8 | CDH6 | cadherin 6, type 2, K-cadherin (fetal kidney) | NM_004932 |
| protein binding-9 | DCBLD2 | discoidin, CUB and LCCL domain containing 2 | NM_080927 |
| protein binding-10 | ENG | endoglin (Osler-Rendu-Weber syndrome 1) | NM_000118 |

TABLE 1g

| | Gene symbol | Gene title | Genbank number |
|---|---|---|---|
| Classification 12 | | | |
| protein modification-1 | SH3RF1 | SH3 domain containing ring finger 1 | NM_020870 |
| protein modification-2 | SMURF2 | SMAD specific E3 ubiquitin protein ligase 2 | NM_022739 |
| protein modification-3 | TFPI2 | tissue factor pathway inhibitor 2 | NM_006528 |
| protein modification-4 | ITGB3 | integrin, beta 3 (platelet glycoprotein IIIa, antigen CD61) | NM_000212 |
| protein modification-5 | MYPN | myopalladin | NM_032578 |
| protein modification-6 | LRP2BP | LRP2 binding protein | NM_018409 |
| protein modification-7 | HECW2 | HECT, C2 and WW domain containing E3 ubiquitin protein ligase 2 | NM_020760 |
| protein modification-8 | PKIA | protein kinase (cAMP-dependent, catalytic) inhibitor alpha | NM_006823 |
| Classification 13 | | | |
| signal molecule-1 | LYPD1 | LY6/PLAUR domain containing 1 | NM_144586 |

TABLE 1g-continued

| | Gene symbol | Gene title | Genbank number |
|---|---|---|---|
| signal molecule-2 | GATA6 | GATA binding protein 6 | NM_005257 |
| signal molecule-3 | RAB27B | RAB27B, member RAS oncogene family | NM_004163 |
| signal molecule-4 | SOX11 | SRY (sex determining region Y)-box 11 | NM_003108 |
| signal molecule-5 | ARHGAP22 | Rho GTPase activating protein 22 | NM_021226 |

TABLE 1h

| Classification 14 | Gene symbol | Gene title | Genbank number |
|---|---|---|---|
| transcription-1 | ETV1 | ets variant gene 1 | NM_004956 |
| transcription-2 | ETV5 | ets variant gene 5 (ets-related molecule) | NM_004454 |
| transcription-3 | FOXP1 | forkhead box P1 | NM_032682 |
| transcription-4 | HMGA2 | high mobility group AT-hook 2 | NM_003483 |
| transcription-5 | KLF12 | Kruppel-like factor 12 | NM_007249 |
| transcription-6 | PRDM16 | PR domain containing 16 | NM_022114 |
| transcription-7 | SIM2 | single-minded homolog 2 (Drosophila) | NM_009586 |
| transcription-8 | SUHW2 | suppressor of hairy wing homolog 2 (Drosophila) | NM_080764 |
| transcription-9 | ENO1 | enolase 1 | NM_001428 |
| transcription-10 | MITF | microphthalmia-associated transcription factor | NM_198159 |
| transcription-11 | TCF3 | transcription factor 3 (E2A immunoglobulin enhancer binding factors E12/E47) | NM_003200 |
| transcription-12 | SMYD3 | SET and MYND domain containing 3 | NM_022743 |

TABLE 1i

| Classification 15 | Gene symbol | Gene title | Genbank number |
|---|---|---|---|
| transport-1 | ATP6V1G3 | ATPase, H+ transporting, lysosomal 13 kDa, V1 subunit G isoform 3 | NM_133262 |
| transport-2 | KCTD16 | potassium channel tetramerisation domain containing 16 | NM_020768 |
| transport-3 | NUPL1 | nucleoporin like 1 | NM_014089 |
| transport-4 | SLC14A1 | solute carrier family 14 (urea transporter), member 1 (Kidd blood group) | NM_015865 |
| transport-5 | SLC16A4 | solute carrier family 16 (monocarboxylic acid transporters), member 4 | NM_004696 |
| transport-6 | SLC4A4 | solute carrier family 4, sodium bicarbonate cotransporter, member 4 | NM_003759 |
| transport-7 | SLC9A7 | solute carrier family 9 (sodium/hydrogen exchanger), isoform 7 | NM_032591 |
| transport-8 | TRPC4 | transient receptor potential cation channel, subfamily C, member 4 | NM_016179 |
| transport-9 | MCFD2 | multiple coagulation factor deficiency 2 | NM_139279 |
| transport-10 | SLC26A4 | solute carrier family 26, member 4 | NM_000441 |
| transport-11 | MCOLN3 | mucolipin 3 | NM_018298 |
| transport-12 | SLC25A37 | solute carrier family 25, member 37 | NM_016612 |
| transport-13 | SLC30A7 | solute carrier family 30 (zinc transporter), member 7 | NM_133496 |

TABLE 1j

| Classification 16 | Gene symbol | Gene title | Genbank number |
|---|---|---|---|
| others-1 | FLJ38725 | hypothetical protein FLJ38725 | NM_153218 |
| others-2 | KIAA1913 | KIAA1913 | NM_052913 |
| others-3 | PHLDB2 | pleckstrin homology-like domain, family B, member 2 | NM_145753 |
| others-4 | PLCXD2 | phosphatidylinositol-specific phospholipase C, X domain containing 2 | NM_153268 |
| others-5 | SAMD3 | sterile alpha motif domain containing 3 | NM_001017373 |
| others-6 | ZNF423 | zinc finger protein 423 | NM_015069 |
| others-7 | FLJ33996 | hypothetical protein FLJ33996 | NM_175894.2 |
| others-8 | PLEKHK1 | pleckstrin homology domain containing, family K member 1 | NM_145307 |
| others-9 | PTOV1 | prostate tumor overexpressed gene 1 | NM_017432 |
| others-10 | FAM40B | family with sequence similarity 40, member B | NM_020704 |
| others-11 | ABI3BP | ABI gene family, member 3 (NESH) binding protein | NM_015429 |
| others-12 | NHS | Nance-Horan syndrome (congenital cataracts and dental anomalies) | NM_198270 |
| others-13 | DTL | denticleless homolog (Drosophila) | NM_016448 |

TABLE 1j-continued

| Classification 16 | Gene symbol | Gene title | Genbank number |
|---|---|---|---|
| others-14 | C1GALT1 | core 1 synthase, glycoprotein-N-acetylgalactosamine 3-beta- | NM__020156 |
| others-15 | CPNE8 | copine VIII | NM__153634 |
| others-16 | TMEM49 | transmembrane protein 49 | NM__030938 |

(2) The method as set forth in (1), wherein the distinguishing marker(s) is at least one of the genes listed the classifications 6, 7, 8, 10, and 13 in Tables 1a to 1j.

(3) The method as set forth in (2), wherein the distinguishing markers are a combination of one or more genes from each of the classifications 6, 7, 8, 10, and 13 in Tables 1a to 1j.

(4) The method as set forth in any one of (1) to (3), wherein the distinguishing marker is at least one of the genes listed in

TABLE 2

| Gene symbol | Gene title | Genbank number |
|---|---|---|
| CHI3L1 | chitinase 3-like 1 (cartilage glycoprotein-39) | NM__001276 |
| FLG | filaggrin | NM__002016 |
| CFI | complement factor I | NM__000204 |
| ANXA10 | annexin A10 | NM__007193 |
| LYPDC1 | LY6/PLAUR domain containing 1 | NM__144586 |
| GATA6 | GATA binding protein 6 | NM__005257 |

(5) The method as set forth in any one of (1) to (4), wherein the detection of the difference in the expressions of the distinguishing markers is carried out by detecting expression of the gene or expression of a protein encoded by the gene.

(6) A microarray for distinguishing mesenchymal stem cells, the microarray including at least one of (a) to (d) immobilized thereon:
  (a) at least one of genes having the base sequences identified with the accession numbers listed in Tables 1a to 1j;
  (b) an antisense chain of at least one of genes having the base sequences identified with the accession numbers listed in Tables 3a to 3j;
  (c) a partial base sequence of (a) or (b); and
  (d) a polynucleotide that is capable of hybridizing, under stringent conditions, with a polynucleotide having the base sequence described in any one of (a) to (c).

(7) An antibody, being inducible with a polypeptide described in (e) or (f), and bindable specifically with the polypeptide specifically:
  (e) a polypeptide encoded by any one of the genes having the base sequences identified with the accession numbers listed in Tables 1a to 1j; and
  (f) a partial polypeptide of the polypeptide described in (e).

(8) A kit for distinguishing and separating mesenchymal stem cells, including any one of (g) to (i):
  (g) a microarray as set forth in (6);
  (h) an antibody as set forth in claim (7); and
  (i) a probe for detecting whether the distinguishing marker gene for mesenchymal stem cells is expressed or not, the distinguishing marker gene comprising a polynucleotide, which, under strigent condition, hybridizes with a gene or a partial sequence thereof, the gene having a base sequence identified with the accession number listed in any one of Tables 1a to 1j.

(9) A method for distinguishing and separating mesenchymal stem cells, the method including:
  separating the mesenchymal stem cells distinguished by a method as set forth in any one of (1) to (5).

(10) A cell-containing composition including:
  mesenchymal stem cells separated by a method as set forth in (9); or
  a multiplied culture of the mesenchymal stem cells.

(11) A drug for regenerative medicine, including:
  a cell-containing composition as set forth in (10).

(12) A distinguishing marker for distinguishing mesenchymal stem cells, the distinguishing marker being at least one of genes having the base sequences identified with the accession numbers listed in Tables 1a to 1j.

(13) A distinguishing marker for distinguishing mesenchymal stem cells, the distinguishing marker being at least one of polypeptides encoded by genes having the base sequences identified with the accession numbers listed in Tables 1a to 1j.

(14) A method of judging whether a sample provider has been developed a disease related with mesenchymal stem cells or whether the sample provider has a possibility of developing the disease in the future, the method judging by treating a sample, which is separated in vivo from the sample provider, with any one or more of:
  a method as set forth in any one of (1) to (5);
  a microarray as set forth in (6);
  an antibody as set forth in (7);
  a kit as set forth in (8); and
  a distinguishing marker as set forth in (12) or (13).

(15) A drug for regenerative medicine, the drug suppressing undifferentiating property of mesenchymal stem cells and comprising siRNA for a gene or a partial sequence thereof, the gene having any one of the base sequences identified with the accession numbers listed in Tables 1a to 1j.

Effect of the Invention

In the method of the present invention for distinguishing mesenchymal stem cells and the use thereof, the distinguishing marker is a gene whose expression pattern in undifferentiated mesenchymal stem cells is clearly different from expression pattern thereof in fibroblasts, osteoblasts, chondrocytes and adipose cells, etc. This makes it possible to distinguish and/or separate, e.g., undifferentiated mesenchymal stem cells contained in marrow from the connective tissue cells exactly accurately, and easily.

Thus, according to the present invention, it is possible to overcome the problems hindering the application of undifferentiated mesenchymal stem cells to the regenerative medicine, the mesenchymal stem cells being pluripotential and being capable of differentiating to bone, cartilages, fats, muscles, tendons/ligaments, nerves, etc. That is, according to the present invention, it is possible to overcome the problem in distinguishing undifferentiating mesenchymal stem cells from other cells such as fibroblasts and connective tissue cells. Thus, the present invention can make a great contribution to regenerative medicine using mesenchymal stem cells.

Moreover, mesenchymal stem cells used by the method of distinguishing the mesenchymal stem cells, and composition containing the same can be applied to a drug for regenerative medicine.

BEST MODE FOR CARRYING OUT THE INVENTION

Figure 1:
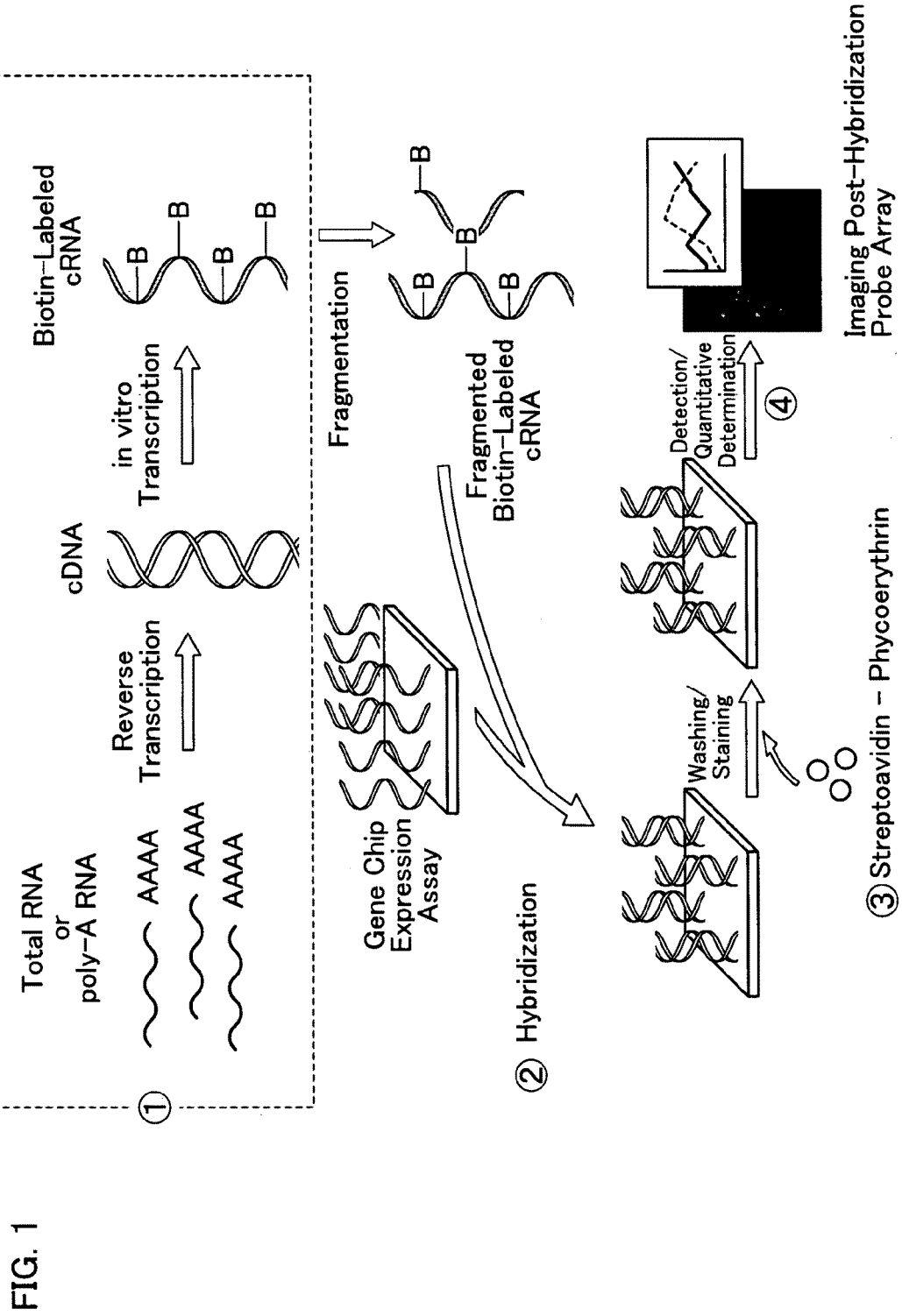
FIG. 1 a view schematically illustrating a flow of procedure of a present Example.

The present invention makes it possible to construct a method of effectively distinguishing and separating mesenchymal stem cells from other cell groups such as connective tissue cells (such as fibroblasts, osteoblasts, chondrocytes, adipose cells) etc. by using a DNA microarray to detect, as a distinguishing marker, a gene that is specifically expressed in undifferentiated stem cells. Use of the present invention makes it possible to perform a qualitative inspection of mesenchymal stem cells multiplied in vitro (on whether the mesenchymal stem cells have differentiation ability or not). This contributes to the practical application of the regenerative medicine using mesenchymal stem cells.

In the following, characteristic features of the present invention, that is, a method of distinguishing mesenchymal stem cells will be described firstly together with explanation on distinguishing/separating marker, microarray, and antibody to be used in the method. Finally, various applied technologies will be described herein such as distinguishing/separating method, cell-containing compositions (which further contain cell secreta (growth factor or the like) preferably), drugs for regenerative medicine, distinguishing/separating kit, and the like.

In this DESCRIPTION, the term "polypeptide" is exchangeable with "peptide" or "protein". The polypeptide in the present invention may be a polypeptide isolated from a natural source, produced recombinantly, or synthesized chemically.

In this DESCRIPTION, the term "polynucleotide" is exchangeable with "gene", "nucleic acid", or "nucleic acid molecule", and intends to mean a polymer of nucleotides. Moreover, what is meant by the term "gene" encompass not only DNA but also RNA (e.g., mRNA). In this DESCRIPTION, the term "base sequence" is exchangeable with "gene sequence", "nucleic acid sequence" or "nucleotide sequence", and the "base sequence" is expressed as a sequence of deoxyribonucleotide (abbreviated as A, G, C, and T).

<1. Method of Distinguishing Mesenchymal Stem Cells>

A method according to the present invention for distinguishing mesenchymal stem cells comprises the step of distinguishing mesenchymal stem cells from the connective tissue cells by detecting a difference between expressions in mesenchymal stem cells and the connective tissue cells by using a distinguishing marker, which is at least one of genes having the base sequences identified with the accession numbers shown in Tables 1a to 1j above. The method according to the present invention is not particularly limited in terms of specific arrangements such as other steps, conditions, materials to use, devices to use, etc.

On Tables 1a to 1j, 139 genes are classified into sixteen classifications according to molecular functions of proteins encoded by the genes, referring to Gene Ontology (GO) of the European Bioinformatics Institute.

Classification 1 is a category for ATP-GTP binding proteins, and 8 kinds of genes with 8 accession numbers belong thereto. Moreover, Classification 2 is a category for binding proteins, and 10 kinds of genes with 10 accession numbers belong thereto. In this DESCRIPTION and Tables, "binding-1~10" means "DNA/metal ion/collagen binding-1~10". Classification 3 is a category for factors relating to cell growth factor or maintenance, and 11 kinds of genes with 11 accession numbers belong thereto.

Classification 4 is a category for cytokine, and 6 kinds of genes with 6 accession numbers belong thereto. Classification 5 is a category for cytoskeleton, and 9 kinds of genes with 9 accession numbers belong thereto. Classification 6 is a category for enzymes, and 3 kinds of genes with 3 accession numbers belong thereto.

Classification 7 is a category for extracellular matrix or cytoskeleton, and 5 kinds of genes with 5 accession numbers belong thereto. Classification 8 is a category for growth factors or receptors, and 7 kinds of genes with 7 accession numbers belong thereto.

Classification 9 is a category for membrane, and 12 kinds of genes with 12 accession numbers belong thereto. Classification 10 is a category for membrane binding proteins, and 4 kinds of genes with 4 accession numbers belong thereto.

Classification 11 is a category for factors relating to protein binding, and 10 kinds of genes with 10 accession numbers belong thereto. Classification 12 is a category for factors relating to protein modification, and 8 kinds of genes with 8 accession numbers belong thereto. Classification 13 is a category for factors relating to signal transduction, and 5 kinds of genes with 5 accession numbers belong thereto.

Classification 14 is a category for transcription factors, and 12 kinds of genes with 12 accession numbers belong thereto. Classification 15 is a category for factors relating to intercellular transport, and 13 kinds of genes with 13 accession numbers belong thereto.

Classification 0.16 is a category for other factors not belonging to any of the above classification, and 16 kinds of genes with 16 accession numbers belong thereto. The categories are classified according to open information disclosed in NCBI.

As described above, the gene groups listed on Tables 1a to 1j are classified in terms of the molecular functions of the proteins encoded by the genes. The use of these genes as distinguishing markers makes it possible to distinguish mesenchymal stem cells from the connective tissue cells by referring to the function or activity of the genes in mesenchymal stem cells and the connective tissue cells. More specifically, for example, if a factor relating to a particular extracellular matrix is expressed at a high expression level in mesenchymal stem cells, while the expression level of the factor is not so high in the connective tissue cells, then the use of a gene belonging to Classification 7 will make it possible to distinguish mesenchymal stem cells easily and exactly.

Moreover, it is advantageous that these genes, which can be used as the distinguishing markers, can be also utilized as markers of mesenchymal stem cells to distinguish them in terms of molecular function.

On Tables 1a to 1j, genes are listed in abbreviation in the column of "Gene symbol". general names and other information of the genes are listed in the column of "Gene title", and the accession numbers in Genbank are listed in the column of "Genbank number". For some genes (such as Transcript variant) that are given plural accession numbers, the scope of the present invention, needless to say, encompasses all genes represented with all the accession numbers.

Moreover, what is meant by the term "connective tissue" in this DESCRIPTION is all supporting and connective tissues encompassing cartilaginous tissue and osseous tissue. The supporting tissues collectively mean the connective tissue in a narrow sense, and specially differentiated connective tissue (cartilaginous tissue, osseous tissue, blood, and lymph). The term "connective tissue" may mean the supporting tissue in a broad sense. Ontogenically, the connective tissue is derived from "mesoblast (or from ectoderm in some cases)" and has functions of supporting an internal structures inside a body. Moreover the term "connective tissue cells" mean cell constructing the supporting and connective tissues. Example of immobilized cells encompass fibroblasts, reticular cells, adipose cells. Example of mobile cells encompass macrophages (histiocyte or macrophage), mast cells, plasma cells, lymphoid cells, granulocytes. Examples of immobilized cells constructing the cartilaginous tissue encompass chondrocytes. Examples of cells constructing osseous tissue encompass Osteoblasts and Osteocytes. It is preferable that the present invention be adopted to distinguish mesenchymal stem cells from fibroblasts, osteoblasts, chondrocytes, and adipose cells (which are collectively referred to as "connective tissue cells" hereinafter") among the various cells mentioned above.

Moreover, the gene groups listed in Tables 1a to 1j, which are used as "distinguishing markers" in the present invention, are genes that have been proved, by an analysis using DNA microarray to study expression profiles in undifferentiated mesenchymal stem cells, fibroblasts, osteoblasts, chondrocytes and adipose cells, that that they have an ability to show significant differences in expression levels between undifferentiated mesenchymal stem cells and other cell groups.

Referring to the difference in the expression level caused by the gene groups, it is possible to distinguish the undifferentiated mesenchymal stem cells from fibroblasts, osteoblasts, chondrocytes, and adipose cells easily, exactly, and accurately. The base sequence of the gene groups in Tables 1 and the amino acid sequence information of the proteins encoded by the gene groups have been publicly known. Especially, the base sequence information of the gene groups are available from the gene data base in the Genbank referring to the accession numbers listed in Tables 1a to 1j.

Moreover, among the genes listed in Tables 1a to 1j, these genes are preferable which satisfy the criteria as described in later-described Examples. For example, genes having high "Fold Average" and "Expression level" are preferably used solely or in combination. Furthermore, it is preferable to use such a gene as a marker that have "Fold Average" of 2 or more, and/or "Expression level" of 0.5 or more.

Moreover, the distinguishing marker is preferably at least one of the genes that belong to the classifications 6, 7, 8, 10, and 13 in Tables 1a to 1j.

The genes that belong to the classifications 6, 7, 8, and 13 in Tables 1a to 1j show greatly different expression patterns especially between mesenchymal stem cells and the connective tissue cells. Most of the genes that belong to the classifications 6, 7, 8, 10, and 13 in Tables 1a to 1j show higher expression level in mesenchymal stem cells. Because of this, the gene that belong to the classifications 6, 7, 8, 10, and 13 in Tables 1a to 1j are preferably applicable as the distinguishing markers. Moreover, the use of such a gene that have a high expression level and show rather stable results with different individuals make it possible to distinguish mesenchymal stem cells exactly.

It is more preferable to use, in combination, one or more gene selected from each classification 6, 7, 8, 10, and 13 in Tables 1a to 1j, that is, to select at least one gene each from the classifications 6, 7, 8, 10, and 13 and to use the genes as the distinguishing marker in combination. By selecting at least one gene from the 5 classifications, it is possible to check the expression pattern for the gene(s) of each of the 5 classifications. This makes it possible to distinguish mesenchymal stem cells more exactly and more accurately.

Moreover, it is especially preferable that at least one gene selected from the genes listed in Table 2 be used as the distinguishing marker.

Table 2 lists 6 genes that are especially preferable among the 139 genes listed in Tables 1a to 1j. The 6 genes show especially greatly different expression patterns between mesenchymal stem cells and the connective tissue cells. Moreover, the 6 genes exhibit high expression levels. Because of these, the 6 genes are most preferably applicable as the distinguishing markers. Moreover, the use of such a small number of marker makes it possible to distinguish mesenchymal stem cells in a more user-friendly manner and with a lower cost.

Furthermore, it is possible to use, in combination, genes belonging to the same one of the 16 classification. For example by using, as the distinguishing marker, a combination of genes belonging to the classification relating to the transcription factor, it is possible to perform evaluation on protein synthesis specific to mesenchymal stem cells even at an early stage of the protein synthesis, or the like property. Moreover, by using a combination of genes belonging to the classification relating to the cell skeleton, it is possible to perform evaluation on protein production (such as production of keratins) etc. characteristic to mesenchymal stem cells, or the like property. Furthermore, by using a combination of genes belonging to the classification relating to growth factors, it is possible to perform evaluation on growth factor production etc. in the cells, or the like property. Moreover, by using a combination of genes belonging to the classification relating to extracellular matrix, it is possible to perform evaluation on adhesiveness of the cells, or the like property. Moreover, by using a combination of genes belonging to the classification relating to signal transduction, it is possible to perform evaluation on responsibility to extracellular stimulus, or the like property. Moreover, by using a combination of genes relating to the transportation, it is possible to evaluate a state of the intracellular transportation, or the like property.

As described above, the effects characteristic to the categories can be attained by using in combination the distinguishing markers classified in the categories respectively. Thus, such a combination of the distinguishing markers classified in the categories respectively is very useful and make it possible to distinguish mesenchymal stem cells more exactly and accurately.

Moreover, apart from the applications described above, it is possible to perform comprehensive analysis, which covers each characteristic of the classifications, by selecting at least one gene from each of 16 classifications (but may be not from the other classifications). In this case, it is sufficient for the distinguishing markers that they include at least one gene from each classification. Especially, the use of a maker with a high "Evaluation Level" described in Examples later, or the use of a greater number of markers will allow distinguishing or analyzing mesenchymal stem cells more exactly and accurately, thereby attaining a more reliable distinguishing method. Thus, the combination of the distinguishing markers is preferable to include the distinguishing markers having higher "Evaluation Levels", and to include as many the distinguishing markers as permitted.

Moreover, the detection of the difference in the expression levels of the distinguishing markers can be carried out by detecting the expression of the genes or the expression of the protein encoded by the genes. More specifically, the present invention can distinguish mesenchymal stem cells from the connective tissue cells by detecting the difference in the expression levels of the distinguishing marker genes as described above, which occurs between mesenchymal stem cells and the connective tissue cells. Thus, the present invention includes a distinguishing marker for mesenchymal stem cells, the distinguishing marker being one of the genes having the base sequences identified with the accession numbers listed in Tables 1a to 1j.

In the present invention, the detection of the expression of the gene groups acting as the distinguishing marker can be performed suitably by a conventionally known method that is applicable to detection of expression of known genes. For example, the detection of the gene groups of the distinguishing markers can be carried out by using a microarray, on which at least one of the followings (a) to (d) are immobilized, for distinguishing mesenchymal stem cells:

(a) at least one of genes having the base sequences identified with the accession numbers listed in Tables 1a to 1j;

(b) an antisense chain of at least one of genes having the base sequences identified with the accession numbers listed in Tables 1a to 1j;

(c) a partial base sequence of (a) or (b); and (d) a polynucleotide that is capable of hybridizing, under stringent conditions, with a polynucleotide having the base sequence described in any one of (a) to (c).

The microarray may be any type of conventionally known microarray such as the DNA microarray of Affymetrix US, a Stanford type DNA microarray, a DNA microarray on which oligonucleotides are directly synthesized chemically on a silica substrate by using fabricating technique, which is used in the semiconductor production. The microarray in the present invention is not particularly limited in terms of its specific size, shape, system, etc.

With the microarray for distinguishing mesenchymal stem cells, it is possible to perform comprehensive and systematic analysis on the expression of the gene groups of many distinguishing markers, and thus it is possible to distinguish mesenchymal stem cells from the connective tissue cells very easily, exactly, and accurately. As such, the microarray for distinguishing mesenchymal stem cells is highly useful. The present invention, therefore, includes the microarray for distinguishing mesenchymal stem cells.

In other words, the method according to the present invention for distinguishing mesenchymal stem cells is preferably arranged such that plural distinguishing markers are used as indicators. Especially, it is preferable to use a combination of plural kinds of distinguishing markers whose expression in mesenchymal stem cells is sufficiently different from that in other cell groups and whose expression level is high. For example, appropriate combinations of CHI3L1, FLG, KRTAP1-5, RGS4, HNT, SLC14A1, IFI30, ZNF423, LXN, whose Fold Average and Expression level are high are preferable.

Moreover, apart from the microarray for distinguishing mesenchymal stem cells, it is possible to use, for example, the northern blotting technique in order to detect the expression of the gene groups of the distinguishing markers according to the present invention. Moreover, in order to detect and distinguish the expression of the gene of the distinguishing marker according to the present invention, a detection probe can be used, which detects a distinguishing marker gene having a base sequence that hybridizes, under stringent conditions, with the whole or part of the DNA sequence of the gene of the distinguishing marker according to the present invention:

It is possible to carry out the detection of the expression of the genes in the mesenchymal stem cells and the connective tissue cells by using the detection probe. For example, a DNA probe of an appropriate length is prepared from a DNA sequence of a gene of a well-known distinguishing marker and labeled with, for example, fluorescence. This DNA probe is hybridized with the analyte, thereby to carry out the detection of mesenchymal stem cells. The detection probe may be a probe for detecting a distinguishing marker gene constituted with the whole or part of an antisense chain of a base sequence of a gene of a well-known marker.

The "stringent conditions for the hybridization of the DNA sequence of the marker gene" with the base sequence of the present invention for preparation of the DNA probe are, for example, to carry out the hybridization at 42° C. followed by washing treatment at 42° C. with a buffer solution containing 1×SSC (0.15M NaCl, 0.015M sodium citrate) and 0.1% SDS (Sodium dodecyl sulfate), or more preferably to carry out the hybridization at 65° C. followed by washing treatment at 65° C. with a buffer solution containing 0.1×SSC and 0.1% SDS (Sodium dodecyl sulfate). Other various factors than the temperature condition would influence the stringency of the hybridization. It is possible for a person skilled in the art to attain stringency equivalent to the exemplified stringency of the hybridization by combining the various factors.

The detection of the expression of the gene of the distinguishing marker in the analyte cells may be preceded by quantitative PCR or semi-quantitative PCR in order to amplify the genes of the analyte cells. The quantitative PCR or semi-quantitative PCR may be RT-PCR (reverse PCR). The quantitative PCR or semi-quantitative PCR is carried out with a pair of sense primer and antisense primer for amplifying the marker gene of the present invention.

Moreover, the method according to the present invention for distinguishing mesenchymal stem cells can be carried out easily by the Invader (Registered Trademark) technique. For example, the method according to the present invention for distinguishing mesenchymal stem cells can be carried out in the following manner: A signal probe, which is designed to have (i) a sequence that hybridizes specifically with the sequence of the distinguishing marker, and (ii) a site cleaved by an enzyme, is reacted with total RNA (or cDNA) extracted from the analyte cells, Invader (Registered Trademark) Oligo, Cleavase (Registered Trademark) Enzyme, and FRET Probe at a predetermined temperature and for a predetermined period (for example, at 63° C. for 2 hours). The following literatures may be referred to for concrete experimental methods and conditions to carry out the method appropriately. Literatures: (i) T. J. Griffin et al., Proc Natl Acad Sci USA 96, 6301-6 (1999), (ii) M. W. Kaiser et al., J Biol Chem 274, 21387-94 (1999), (iii) V. Lyamichev et al., Nat Biotechnol 17, 292-6 (1999), (iv) R. W. Kwiatkowski et al., Mol Diagn 4, 353-64 (1999), (v) J. G. Hall et al., Proc Natl Acad Sci USA 97, 8272-7 (2000), (vi) M. Nagano et al., J Lipid Res 43, 1011-8 (2002), (vii) etc. The use of the invader technique would eliminate the need of gene amplification, and thus can be performed fast and at low costs. The use of a commercially-available invader kit makes it more easy to carry out the present invention.

Moreover, the method according to the present invention for distinguishing stem cells may be carried out by in situ hybridization. For example, molecular hybrid of the sample of the analyte cells on a slide glass may be directly formed by using the distinguishing marker or a material labeled with a part of the sequence thereof may be used as a probe. More specifically, a thin specimen (paraffin segment, frozen segment, etc.) of the analyte cell is prepared on a slide glass and hybridized with the labeled probe. Then, the specimen is exposed after the probe is washed away and a photographic emulsion is applied on the specimen in the same manner as in the northern hybridization technique. After development, the hybridized portion is identified from silver particle distribution. The following literatures may be referred to for concrete experimental methods and conditions to carry out the method appropriately. Literatures: (i) "in situ hybridization technique (July, 1995), edited by Toshiyuki FURUSHO and You IMURA, published by Kanehara & Co., Ltd., pages 932 to 937, and (ii) "Analysis of gene expression by in situ hybridization technique" "Gene Engineering Experiments (May, 1991), written by Shintaro NOMURA, published by Japan Radioisotope Association, pages 221 to 232, (iii) etc. There are two types of the in situ hybridization technique: one adopts auto radiography to detect a site at which a DNA probe labeled with a radio isotope (mainly 3H) is located, and the other adopts fluorescent microscopy to detect fluorescent signal from the labeled DNA probe. Either technique is applicable to the present invention.

In case where the detection of the expression of the gene of the distinguishing maker according to the present invention is carried out by detecting the protein encoded by the gene, distinguishing mesenchymal stem cells may be carried out by detecting the expression of the distinguishing marker protein in mesenchymal stem cells and connective tissue cells with an antibody prepared from the protein, which antibody binds with the protein specifically.

Therefore, distinguishing marker for distinguishing mesenchymal stem cells is included, which is any one of polypeptides encoded by the genes having the base sequences identified with the accession numbers listed in Tables 1a to 1j. Moreover, an antibody is included, which is inducible with a polypeptide described in (e) or (f) and bindable specifically with the polypeptide:

(e) a polypeptide encoded by any one of the genes having the base sequences identified with the accession numbers listed in Tables 1a to 1j; and (f) a partial polypeptide of the polypeptide described in (e).

The antibody may be a polyclonal antibody or a monoclonal antibody. For example, by any standard method conventionally known in the art, the antibody may be prepared against an antigen that is a whole or partial sequence of the polypeptide encoded by the gene of the distinguishing marker of the present invention.

For example, the monoclonal antibody may be prepared in any method. For example, the monoclonal antibody may be obtained from antibody-producing hybridoma prepared by fusing mouse splenetic lymphocytes and mouse-derived myelocytes, each of which are obtained from a mouse immune with the antigen. The hybridoma may be prepared by any conventionally known method such as hybridoma technique (Kohler, G. and Milstein, C., Nature 256, 495-497 (1975)), trioma technique, human B-cell hybridoma technique (Monoclonal Antibodies and Cancer Therapy, Alan R Liss, Inc., 77-96 (1985)).

The antigen is not particularly limited, provided that it is a polypeptide. The antigen may be an antigenic protein, which is formed by binding an antigen determinant substance with a carrier protein. More specifically, the antibody cannot be produced if the antigen is a hapten, which does not have an ability of inducing the antibody production etc. However, the antibody production can be induced by immunizing with antigenic protein prepared by covalent bonding the antigen with a carrier, which is a bio-macromolecule such as a heterogeneous protein. The carrier is not particularly limited and various proteins conventionally known in this field such as ovalbumin, γgloblin, hemocyanin, etc. may be the carrier. Moreover, the monoclonal antibody may be produced transgenically or by the like method.

Moreover, the preparation of the polyclonal antibody may be carried out by purifying an antibody component from a body fluid of an experimental animal inoculated and sensitized with the antibody. Moreover, the animal to be immunized may be a conventionally known experimental animal such as a mouse, rat, rabbit, monkey, hours, etc., and is not particularly limited. Moreover, the inoculation and sensitization with the antigen may be carried out with intervals or quantities which are adopted in a standard method known in this art.

Immunologic measuring methods for well-known antibodies may be adopted to detect the expression of the protein of the distinguishing marker in the analyte cells by using the antibody according to the present invention. Immunologic measuring methods may be a known immunologic measuring method such as RIA method, ELISA method, fluorescent antibody technique, etc. Moreover, besides the above methods, western blotting technique, enzyme immunoassay, observation of coagulation, precipitation, hemoclastic reaction caused by the antibody, morphological detecting methods such as tissue immunostaining, cell immunostaining may be adopted, if necessary.

In the present invention, the detection of the difference in the expression levels of one distinguishing marker may be performed to distinguish mesenchymal stem cells from the result thereof. In order to distinguish mesenchymal stem cells more exactly and more accurately, it is preferable that the differences of the expression levels of plural distinguishing markers be used as indicators. This is another reason why the use of the microarray for distinguishing mesenchymal stem cells is preferable in the case where the difference in the expression levels of one distinguishing marker is used as the indicator.

<2. Method of Distinguishing and Separating Mesenchymal Stem Cells>

The method according to the present invention for distinguishing and separating should include the step of separating mesenchymal stem cells identified by the method of distinguishing the mesenchymal stem cells as described in Item <I>, and is not particularly limited in terms of specific arrangements such as steps other than this step, conditions, materials to use, apparatuses to use, etc.

In the present invention, the separation of mesenchymal stem cells may be carried out by using a Fluorescence-Activated Cell Sorter (FACS), for example. More specifically, mesenchymal stem cells are labeled with the antibody according to the present invention by fluorescent antibody technique. Then, whether or not the polypeptide of the distinguishing marker of mesenchymal stem cells is expressed in the analyte cells is detected. Referring to the detection, mesenchymal stem cells are distinguished and separated. The labeling of undifferentiated mesenchymal stem cells by the fluorescent antibody technique can be done by direct fluorescent antibody technique, or indirect fluorescent antibody technique. In the direct fluorescent antibody technique, an antibody, which specifically binds with the polypeptide of the distinguishing marker according to the present invention, is labeled with fluorescent, and then binds with mesenchymal stem cells, in which the antigen is expressed, thereby to label mesenchymal stem cells. In the indirect fluorescent antibody technique, mesenchymal stem cells, in which the antibody is express, bind with an unlabelled specific antibody of the present invention. And then, a labeled secondary antibody (anti-immune globulin antibody) is bound thereto. The mesenchymal stem cells labeled in these manner can be examined and separated by flow cytometry. The separated sample may be collected via a filter and obverted via epifluorescent microscope for confirmation.

Moreover, apart from FACS, the separation can be done by a Magnetic Cell Sorting (MACS) system. MACS uses an antibody labeled with a magnetized microbeads instead of fluorescent labeling. The targeted cells are specifically labeled with the antibody labeled by the magnetized microbeads for MASC, and then applied to a separating column disposed to a strong permanent magneto. A strong magnetic field produced in the separating column holds the magnetically labeled cell in the separating column but lets the unlabeled cells pass through the separating column. The cells held in the separating column is eluted from the separating column by removing the separating column out of the strong magnetic field. Thereby, mesenchymal stem cells are separated.

Furthermore, the method of the present invention may include the step of concentrating the sample by using a membrane filter or condensation prior to the step of separating by FACS, MACS, or the like.

<3. Distinguishing/Separating Kit>

A kit according to the present invention for distinguishing/separating mesenchymal stem cells should comprise any one of materials described respectively in (g) to (i), and is not particularly limited in terms of other materials, constituent components, etc.:

(g) the above-described microarray for distinguishing mesenchymal stem cells;

(h) the above-described antibody; and (i) the probe for detecting whether the distinguishing marker gene for mesenchymal stem cells is expressed or not, the distinguishing marker gene comprising a polynucleotide, which, under strigent condition, hybridizes with a gene or a partial sequence thereof, the gene having a base sequence identified with the accession number listed in any one of Tables 1a to 1j.

The kit is for easily performing the method of distinguishing mesenchymal stem cells described in Item <1>, or the method of distinguishing/separating mesenchymal stem cells described in Item <2>. The kit can be easily commercialized by comprising any one of materials described respectively in (g) to (i).

Moreover, as described above, it is preferable for greater exactness and accuracy to perform the above methods with plural ones of the distinguishing markers listed in Tables 1a to 1j. Thus, it is preferable for the kit according to the present invention to comprising plural ones of the distinguishing markers. For example, as described in Item <I>, various combination of the genes may be selected and used as a distinguishing marker kit.

As described above, the combination of the distinguishing markers makes it possible to distinguish and separate mesenchymal stem cells more exactly and accurately compared with the single use of the distinguishing marker.

<4. Cell-Containing Compositions and Drugs of Regenerative Medicine>

A cell-containing composition according to the present invention should comprise mesenchymal stem cells separated by the method of distinguishing and separating mesenchymal stem cell described in Item <2>, or mesenchymal stem cells thus obtained and then multiplied. The cell-containing composition according to the present invention is not particularly limited in terms of other arrangements such as compositional arrangement (buffer liquid, culture liquid, or the like), cell number, etc. Moreover, the cell-containing composition according to the present invention preferably contains a secreta (e.g., growth factor, or the like) secreted from cells contained in the cell-containing composition.

The cell-containing composition comprises undifferentiated mesenchymal stem cells capable of differentiating to bones, cartilages, fats, muscles, tendons/ligaments, nerves, etc. Thus, the cell-containing composition can be used as a drug (pharmaceutical composition) for regenerative medicine. That is, a drug according to the present invention for regenerative medicine is not limited particularly in terms of other specific arrangements, provided that it comprises the cell-containing composition. For example, the use of the drug may be such that the undifferentiated mesenchymal stem cells are differentiated to cells of a kind as suitable for the use, and then used. More specifically, this may be carried out in such a manner that the mesenchymal stem cells are differentiated to osteoblasts, chondrocytes and adipose cells, muscle cells, nerve cells, etc. by using a differentiation inducing material such as a cytokine or the like, and then the differentiated calls are administered to a patient to be treated with the regenerative medicine. Therefore, the present invention encompasses drugs for regenerative medicine containing a cell composition obtained by differentiation of the undifferentiated mesenchymal stem cells, apart from the drugs containing the undifferentiated mesenchymal stem cells.

Moreover, administration conditions of the drug for regenerative medicine in actual clinical applications may be determined as appropriate by animal experiments or the like performed as standard methods in this field. That is, the conditions suitable for prevention or therapeutic effects may be determined via animal experiments to study the administration conditions such as dosage, administration intervals, administration routes, etc. The drug for regenerative medicine can be utilized as a drug for "regenerative medicine by cell transplantation" which regenerates a tissue lost by a disease or impairment and resumes a function, which tissue cannot be regenerated by a conventional therapeutic method.

The drug for regenerative medicine is not limited to treatment of a particular disease, symptom, clinical profile, or the like, provided that the drug is used for the purpose of "regenerative medicine by cell transplantation". More specific examples of the drug for regenerative medicine include transplantation of marrow mesenchymal stem cells to a patient of lower limb ischemia (Buerger's disease), transplantation of marrow mesenchymal stem cells to a patient of a periodontal disease, transplantation of marrow mesenchymal stem cells to a patient of osteoarthritis, transportation of amniotic epithelium sheet to burn injured portion, transportation of amniotic stem cells to a patient of diabetes mellitus, and the other transplantation.

The drug for regenerative medicine may be used as a composition by mixed with a pharmaceutically allowable carrier. Examples of the carrier encompass sterilized water, physiological saline, buffers, plant oil, emulsifiers, suspending agents, salts, stabilizers, preservatives, surfactants, release controllers, other proteins (BSA etc.), transfection reagents (encompassing lipofection reagents, liposome, and the like), and the like. Moreover, the following carriers are applicable in the present invention: extracellular matrixes such as glucose, lactose, gum Arabic, gelatin, mannitol, starch paste, magnesium trisilicate, talc, corn starch, keratin, colloid silica, potato starch, urea, hyaluronic acid, collagen, etc.; polylactose, calcium phosphate carrier, etc.

The drug may have any form. For example, the drug may have forms of solution (injection-type), microcapsule, tablet, and the like. The drug may be administered systematically or locally. The local administration is preferable if the systematic administration is side effective or is not so effective as the local administration.

Moreover, the drug may be administered to a patient in any way and the administration may be, for example, surgical, percutaneous, transbronchial, muscular, interperitoneal, intravenous, intra-articular, subdermal, medullary, intracerebroventricular, or oral. The drug may be systematically administered or locally. The local administration to lesion section is preferable if the systematic administration is side effective. Dosage and the way of administration may be varied depending on weight, age, and symptom of the patient, therapeutic purpose, and tissue mobility of the active constituents of the drug, and the other factors. A person skilled in the art can arbitrarily select the dosage and the way of administration.

The therapeutic treatment targets human basically, but may target pet animals (pets) apart from human. Examples of the pet animals encompass non-human mammals such as mice, rats, rabbits, cats, dogs, monkeys, horses, sheep, cows, etc. and other spinal animals.

Moreover, the drug according to the present invention is preferably arranged such that the mesenchymal stem cells or cells differentiated from the mesenchymal stem cells, which are contained therein, be derived from the individual targeted by the therapeutic treatment. However, for the sake of mass production and the other factors, the drug according to the present invention may be arranged such that the mesenchymal stem cells or cells differentiated from the mesenchymal stem cells, which are contained therein, be not derived from the individual targeted by the therapeutic treatment (that is, allogeneic cell). In this arrangement, the immune reaction should be inhibited by a standard method such as use of an immune reaction inhibitor or the like.

<5. Other Use>

It has not been understood which part of the body mesenchymal stem cells are present in vivo (e.g., in marrow). However, the use of the antibody according to the present invention makes it possible to study which part of the body the mesenchymal stem cells are present. Therefore, the technique of the present invention can be applied to development of new medicines or the like. More specifically, if it is understood how the mesenchymal stem cells move or migrate to the lesion section in vivo, it is possible to develop a medicine to contain an active constituent for promoting movement or migration of the mesenchymal stem cell to the lesion.

By using, solely or in combination, a method according to the present invention for distinguishing mesenchymal stem cells, a microarray according to the present invention for distinguishing mesenchymal stem cells, an antibody according to the present invention, and a kit according to the present invention for distinguishing/separating mesenchymal stem cells, it is also possible to judge whether a mesenchymal stem cell-related disease has been developed or whether there is a possibility that such a mesenchymal stem cell-related disease will be developed. This judging method is applicable to both prevention and diagnosis of the diseases.

Applying the present invention to treating a sample separated from a living body is preferred to applying the present invention to treating a human body directly. The sample separated from the living body can be obtained from the human body by a standard method in this field. Examples of such a sample encompass cells (which encompass mesenchymal stem cells) obtained from marrow liquids, peripheral bloods, cord bloods, adipose tissues, periosteum, muscles, synovial membrane, oral cavity tissue. Especially, it is preferable that the biosample contain mesenchymal stem cells be obtained by any one of the methods disclosed in Patent Citations 1 to 3. It is preferable that the sample contain mesenchymal stem cells.

This judging method can be applied to judging whether an examined person has developed a disease or how much possibility of developing the disease in the future the examined person has, for example, by finding the gene expression profiles of the distinguishing marker of the mesenchymal stem cells in a healthy person and a patient of the disease in advance and comparing an expression profile of the mesenchymal stem cell in the examined person (patient) with the gene expression profiles of the healthy person and the patient of the disease to find which of the gene expression profiles of the healthy person and patient the expression profile of the examined person (patient) is similar. In this DESCRIPTION, the "healthy person" is a person who does not have the disease to be examined, and the "patient of the disease" is a person who has the disease. The method according to the present invention for judging whether a disease has been developed or not, may use the method for distinguishing mesenchymal stem cells or the like in other manners than the above arrangement, and may be appropriately modified to use a standard method in this field as of filing of the present application.

The "disease related with mesenchymal stem cells" encompasses any diseases which are caused (that is, "regeneration impairment syndromes) caused in relation to the mesenchymal stem cells such as conventionally known abnormality in mesenchymal stem cells or in differentiation from mesenchymal stem cells. For example, the disease may be a disease targeted by "regenerative medicine by cell transplantation" to regenerate a tissue lost by a disease or impairment and thereby to regain the function, a disease caused by a quantitative reduction in mesenchymal stem cells (abnormality in the number of cells or the like abnormality) or by a qualitative degradation in mesenchymal stem cells (abnormality in the differentiation ability or the like abnormality), that is, by shortage of supply of mesenchymal stem cells, and the like disease. Specific examples of the disease encompass lower limb ischemia (Buerger's disease), periodontal disease, osteoarthritis, intractable skin disease, diabetes, osteoporosis, ischemic heart disease, liver disease, kidney disease, neurodegenerative (Alzheimer disease etc.), and the like.

Osteoarthritis is an example of the disease caused by the shortage of the supply of mesenchymal stem cells. It is deduced that osteoarthritis is caused by quantitative abnormality in mesenchymal stem cell in vivo (more specifically, reduction in the number of the mesenchymal stem cells) due to various factors such as aging, life style, etc. Thus, it is expected that the use of the distinguishing method according to the present invention or the like makes it possible to grasp the quantitative change in mesenchymal stem cell in vivo so as to judge whether a disease has been developed or not and so as to prevent the development of the disease. That is, the quantitative change in mesenchymal stem cells can be detected by using the distinguishing method according to the present invention, the distinguishing marker, or the like. Thus, it is expected that the use of this technique makes it possible to diagnose whether or not there is a possibility of developing a disease that is caused by the shortage of the supply of mesenchymal stem cells. More specifically, for example, a biosample is obtained from the examined person (patient) on a regular basis (at intervals of a few months to few years) to be examined on the quantitative change in mesenchymal stem cells in the biosample by using the distinguishing method of the present invention or the like. The result of the examination of the examined person is compared with the results of examinations in quantitative changes in the mesenchymal stem cells in a healthy person and a patient of osteoarthritis. The examinations of the healthy person and the patient of the disease are performed in advance and in the same manner as the examination of the examined person. The comparison allows exact and accurate diagnosis of whether the examined person has developed osteoarthritis, or has a possibility of developing osteoarthritis in the future.

Moreover, the present invention encompasses drugs for regenerative medicine for suppressing undifferentiating property of mesenchymal stem cells, the drugs comprising siRNA corresponding to the genes having the base sequences identified with the accession numbers listed in Tables 1a to 1j, or to the partial sequences thereof. They are drugs for reducing the undifferentiating property of the mesenchymal stem cell by using RNAi. In other words, the drugs are drugs for regenerative medicine for suppressing the undifferentiating property of mesenchymal stem cell by using RNAi/siRNA by using the genes having the base sequences identified with the accession numbers listed in Tables 1a to 1j, or to the partial sequences thereof.

With the drug for regenerative medicine, it is possible to suppress the undifferentiating property of mesenchymal stem cells certainly and efficiently. Thus, the drug for regenerative medicine is highly beneficial for the regenerative medicine.

The embodiments of the present invention are described in further detail via the following Examples. Needless to say, the present invention is not limited to these Examples. The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

In the present Examples, the following cells were examined in their gene expression profiles: three lines of human fibroblasts (hereinafter, may be referred to as "FB"), three lines of mesenchymal stem cells (hereinafter, may be referred to as "MSC"), three lines of osteoblasts (hereinafter, may be referred to as "OS"), three lines of chondrocytes (hereinafter, may be referred to as "CH"), three lines of adipose cells (hereinafter, may be referred to as "AD"). The osteoblasts, chondrocytes, and adipose cells were prepared by differentiation from the mesenchymal stem cells in vitro.

(0) Differentiation and Collection of Total RNA

Firstly, mesenchymal stem cells were differentiated to adipose cells, chondrocytes, or osteoblasts, and then total RNA was collected. More specifically, these differentiations were carried out as follows.

(0-1) Differentiation to Adipose Cells and Collection of RNA

Media having the following compositions were used as basal medium, adipose differentiation inducing medium, and adipose differentiation maintenance medium.

Adipose Differentiation Inducing Medium
Basal Medium: DMEM (Sigma: D5796, high glucose=4500 mg/L)
Additives: 10% (V/V) FBS (Hyclone, Lot No.: ANC18139)
Penicillin-Streptomycin (Sigma: P0781)
The followings were added freshly (to add the quantities in two weeks).
Insulin: 10 µg/mL (10 mg/mL acetic acid aqueous solution stock) (Wako: 090-03446)

Dexamethason: 1 µM (10 mM EtOH stock) (Sigma: D4902)
Indomethacin: 200 µM (2000 mM DMSO stock) (Wako: 097-02471)
3-isobutyl-1-methylxanthine: 500 µM (1000 mM DMSO stock) (Wako: 537-72353)

Adipose Differentiation Maintenance Medium
Basal Medium: DMEM (Sigma:#D-5796, high glucose=4500 mg/L)
Addition: 10% (V/V) FBS (Hyclone, Lot No.: ANC18139)
Penicillin-Streptomycin (Sigma: P0781)
The following was added freshly (to add the quantities in two weeks).
Insulin: 10 µg/mL (10 mg/mL acetic acid aqueous solution stock) (Wako: 090-03446)
After two weeks were past, L-glutamine: 2 mM (200 mM PBS stock) (Sigma: G3126) was added to the medium. After that, the addition thereof was repeated every two weeks.

After MSC became confluent, the MSC was cultured for 11 days in total by repeating 2-day incubation in the adipose differentiation inducing medium and three-day incubation in the adipose differentiation maintenance medium via medium replacement. Then, total RNA was collected. The medium replacement is carried out by dropping a new medium gently to a surface of 10% residue of an old medium. All the additives were freshly added when the media were replaced.

The RNA extraction after the adipose differentiation was carried out in the following manner. Firstly, the cells were prepared via 11-day adipose differentiation (in φ 100 mm dish). Next, the medium was removed by suction, and the cells were washed with PBS twice. Then, the cell was homogenized with TRIzol (Registered Trademark) (4000 µL/φ 100 mm dish) by using a 21 G needle and 1 ml syringe. After that, chloroform was added thereto in a ¼ quantity thereof, the culture was stirred by Vortex, and then stood still for 20 minutes at room temperatures. Next, the culture was centrifuged at 14000 rpm for 20 minutes at room temperatures (Tomy, MCX-150). Then, a supernatant thereof was transferred into Eppendorf tube, in which 70% EtOH (prepared with RNas free water) of a quantity equivalent to the supernatant was added thereafter. Then, 700 µl of a sample thus prepared was applied into a RNesay (registered trademark) Mini column, and vacuum was applied to the column (Qiagen, QIAvac 24). This was repeated until the whole sample was consumed (2 column/one φ 100 mm dish). The above process was carried out according to the Manual attached to the RNeasy kit. Finally, RNA purification was carried out with a kit (#1906) produced by Ambion.

(0-2) Differentiation to Chondrocyte and Collection of RNA

The chondrocyte differentiation inducing medium had the following composition.

Chondrocyte Differentiation Inducing Medium
αMEM (Sigma:#4526)
Penicillin Streptomycin: (Sigma: #P0781)
L-glutamine: 2 mM (stock sol 200 mM PBS) (Sigma: #G3126)
Dexamethason: $10^{-7}$ M (stock sol 1 M EtOH) (Sigma: #D-1756)
Ascorbate 2-phosphate: 50 µg/ml (stock sol 50 mg/ml MQ) (Sigma: #A-8960)
D-(+)-glucose: 4.5 g/l (stock sol 450 g/l) (Sigma: #G-8769)
Pyruvate: 100 µg/ml (stock sol 100 mg/ml MQ) (Sigma: #28-4020-2)
ITS-plus: 1%% (V/V) (insulin 6.25 µg/ml, transferring 6.25 µg/ml, selenous acid 6.25 µg/ml, linoleic acid 5.33 µg/ml, bovine serum albumim 1.25 mg/ml) (BD: #354352)

TGF-β3: 10 ng/ml (stock sol 10 μg/ml HCl 4 mM, HSA or BSA 1 mg/ml) (Pepro Tec ECL Ltd #100-36)

The chondrocyte differentiation inducing medium of the quantity was added in two weeks. Moreover, TGF-β3 was not added initially: it was added freshly at medium replacement.

Culturing in the chondrocyte differentiation was carried out by pellet incubation technique. More specifically, the culturing was carried out with the inoculation in a density of $2.5 \times 10^5$ cells/tube, and an initial quantity of the chondrocyte differentiation medium of 0.5 ml per tube. After the inoculation, the medium was centrifuged (500 g×5 min). Then, from Day 0 on which the cells were inoculated, the medium was incubated for 28 days via medium replacement performed every 3 days. The first medium replacement reduced the quantity to 1 ml per tube.

RNA extraction was carried out in the following manner. Firstly, the cells were prepared via 28-day chondrocyte differentiation (6 pellets or more). Then, the medium was removed by suction, and then 0.4 ml of PBS was added in the pellets, and then sucked. After 0.2 ml of TRIzol (Registered Trademark) (Invitrogen: 15596-018) was added to each tube, grinding extraction was performed with pellet pestle and silica powder. Then, it was further added in a quantity of 0.8 ml/tube, and the extracted was transferred to tubes. Then, the extracted was treated with chloroform and ethanol. After that, it was treated with RNeasy kit. Thereafter, the process of the extraction was identical with that of the adipose differentiation.

(0-3) Differentiation to Osteoblast and Collection of RNA

The osteoblast differentiation inducing medium had the following composition.

Basal Medium

DMEM (Sigma D6046)

FBS (Hyclone) (Bovine Fetal serum) of 10% Final Concentration

Antibiotic: penicillin-streptmycin (Sigma:P0781)

Osteoblast Differentiation Inducing Medium

DMEM (Sigma D6046 containing glucose 1000 mg/L)

FBS (Hyclone) of 10% Final Concentration

Dexamethason (Sigma D-1756) of $10^{-7}$M Final Concentration

β-glycerophosphate (Tokyo Chemical Industry Co., Ltd. G-0195) of 10 mM Final Concentration Ascorbate 2-phosphate (Sigma: A-8960) of 50 μg/ml Final Concentration added every two weeks L-glutamine of 2 mM Final Concentration added every two weeks Antibiotic: penicillin-streptmycin (Sigma:P0781)

As a referential literature, referred to was "Osteogenic differentiation of purified culture-expanded human, mesenchymal stem cell in vitro." Jaiswal N. J. et al., Cell Biochem. 64, 295-312, 1997.

Firstly, a surface of a culture plate was soaked with 0.01% Collagen type 1 solution (functional peptide IFP9660) overnight. After the solution was removed therefrom, the plate was washed with PBS (phosphate buffered saline) twice. Next, the cells were inoculated on the basal medium for mesenchymal stem cells (10000 cell/cm$^2$). After the cells were incubated to be confluent (in 2 to 3 days after the inoculation), the medium was replaced with the osteoblast differentiation inducing medium (Day 0). After 28-day incubation from Day 0 replacing the osteoblast differentiation inducing medium every 3 days, total RNA was collected. The collection of total RNA was carried out in the same manner as in the adipose cells.

An outline of the flow of the experiment after the collection of total RNA is illustrated in FIG. 1.

(1) cDNA/cRNA Synthesis

Firstly, double stranded cDNA was synthesized from the sample RNA using T7 oligo dT primer. Next, cRNA was synthesized from the double stranded cDNA by in vitro Transcription reaction. In the synthesis of cRNA, the sample was labeled by incorporating biotin-labeled ribonucleotide therein.

(2) Hybridization

Next, the biotin-labeled cRNA was fragmented and hybridized with GeneChip (Registered Trademark: Affymetrix) probe array.

(3) Fluorescent Labeling

After the array hybridized overnight was washed, streptoavidin-phycoerythrin was added therein thereby labeling the sample with fluorescent.

(4) Scanning/Data Analysis

Finally, the fluorescent-labeled array was scanned to capture a non-photographic image, which was then analyzed by special analysis software so as to perform signal digitalization and expression analysis.

The steps (1) to (4) were done by analysis service provided from KURABO, using the DNA microarray "GeneChip (registered trademark)" produced by Affymetrix. The analysis service performs the analysis of a provided sample RNA with GeneChip (registered trademark). Because a person skilled in the art can understand the steps (2) to (4) by referring to KURABO's analysis service, the explanations on the steps (2) to (4) are omitted here.

In the present Example, the GeneChip (registered trademark) was Human Genome U133 Plus 2.0 Arrays (HG-U133 Plus 2.0). Moreover, the GeneChip analysis conditions of the analysis service in the present Example were as follows.

Biotin-labeled target was prepared initially with 2 μg of total RNA. Its analysis protocol is described in One-cycle Target Labeling, GeneChip Expression Analysis Technical Manual, 701021 Rev.5, Section 2 Eukaryotic Sample and Array Processing, Chapter 1 Eukaryotic Target Preparation.

Analysis protocol of the hybridization/scanning is described in GeneChip Expression Analysis Technical Manual, 701021 Rev.5, Section 2 Eukaryotic Sample and Array Processing, Chapter 2 Eukaryotic Target Hybridization. A hybridization oven used herein was Hybridization Oven 640 110V (Affymetrix 800138). A washing/staining apparatus used herein was Fluidies Station 450 (Affymetrix 00-0079). A scanner used herein was GeneChip Scanner 3000 (Affymetrix 00-0074). Software used herein was GeneChip Operating Software ver1.1 (Affymetrix 690036).

Analysis protocol of analysis and digitalization of the scanned image is described in GeneChip Expression Analysis Technical Manual, 701021 Rev.5, Section 2 Eukaryotic Sample and Array Processing, Chapter 3 Washing, Staining, and Scanning. Software used herein was GeneChip Operating Software ver1.1. Algorism used herein was Statistical. Analysis parameters at creating a CIIP file were Scaling Factor; 1, Target Value; 500, Detection Call; Alpha1=0.05, Alpha2=0.065, and Tau=0.015.

The data of analysis and digitalization of the scanned image was obtained by the scanning/data analysis of (4) and processed by "GeneSpring" (Product Name, Trademark) so as to prepare a gene list or the like. The software "GeneSpring" was used according to the manual attached therewith.

That is, gene expression profiles of various genes related to 54675 human genes (probes) were analyzed in the present Example. More specifically, RNAs were collected from cells of 15 lines and analyzed with the DNA microarray in terms of the expression levels for 54675 human genes (probes). The 15 lines were 3 lines of mesenchymal stem cells (MSC) having the ability of differentiating to various cells, 3 lines of the cells (OS) obtained from the bone differentiation of MSC, 3 lines of the cells (CH) obtained from the cartilage differentiation, 2 lines of the cells (AD) obtained from the adipose differentiation, and 3 lines of fibroblasts (FB) derived from skin and gingiva, which fibroblasts did not have the ability of differentiating to various cells.

Figure 2:
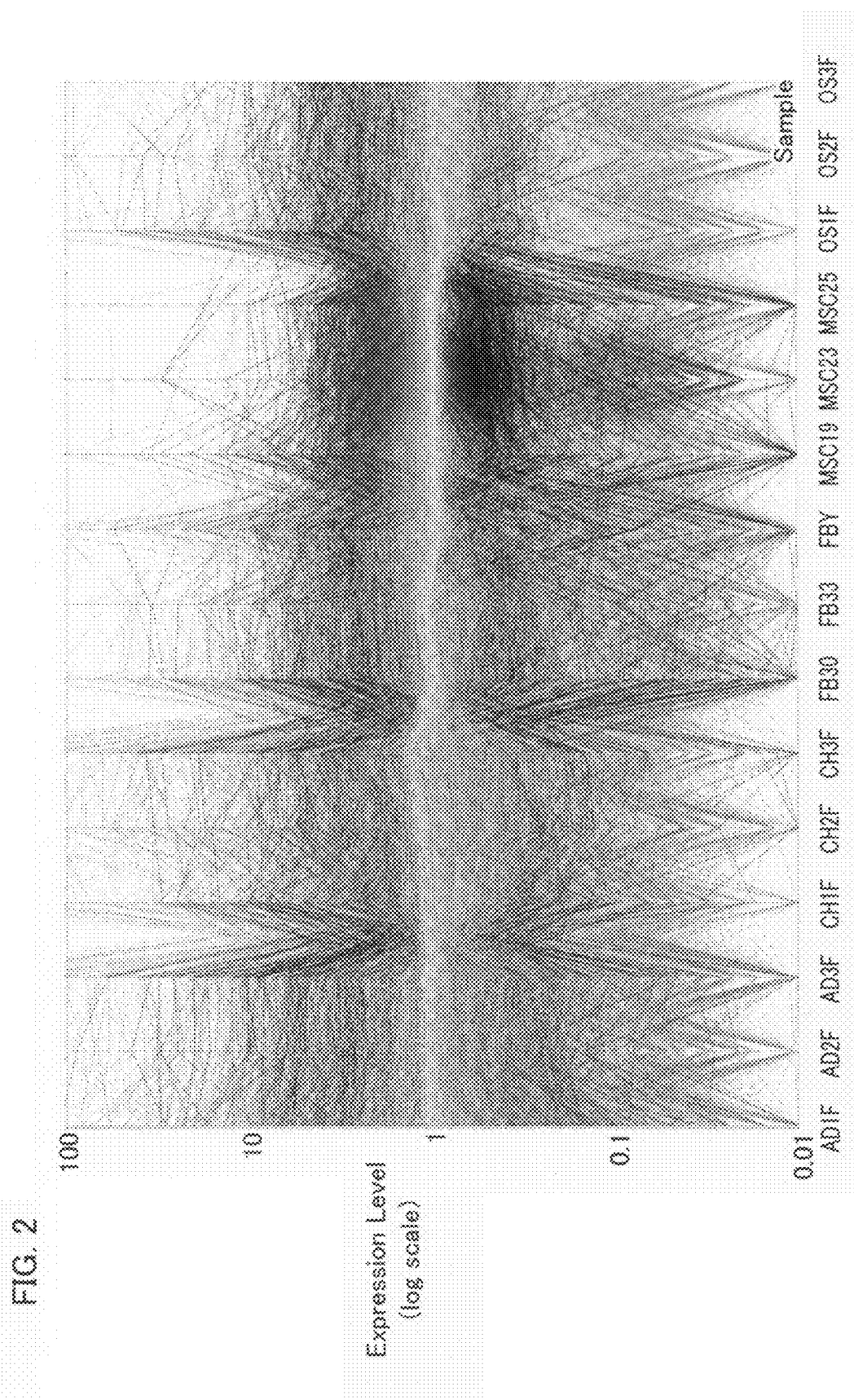
FIG. 2 is a view illustrating result of analysis to analyze a difference in expression of genes between mesenchymal stem cells (MSC) and other connective tissues by using a DNA microarray in a present Example.

The analysis results are illustrated in FIG. 2. Each curves represents one gene (probe) in FIG. 2 (that is, there are 54675 curves in FIG. 2) where the vertical axis represents the gene expression intensities and the horizontal axis represents cells, which are, from the left, AD (3 lines) obtained from the adipose differentiation, CH (3 lines) obtained from obtained from the cartilage differentiation, FB (3 lines) of skin and gingiva, stem cells MSC (3 lines), and OS (3 lines) from bone differentiation. It should be noted that the same kind of cells such as the left most 2 lines of AD obtained from adipose differentiation tend to show the same expression level, and thus tend to be plotted in parallel with, each other.

Moreover, when FIG. 2 is shown in color, the curves are colored according to the expression in such a way that red represents genes expressed at high levels in MSC, blue represents genes expressed at low levels in MSC, and yellow represents genes expressed at medium levels in MSC. When FIG. 2 is shown in black and white, this information is not given.

The genes in red in 3 lines of MSC in the middle but on the right side of FIG. 2 but show low expression intensities in other cell types are applicable as undifferentiating markers specific to MSC. That is, genes having such expression profiles that "the expression level is high in MSC but low in the other cells" were selected and identified as the undifferentiating markers specific to MSC, the markers being capable of differentiating mesenchymal stem cells from bone, cartilage, adipose, and fibroblast. The selection of the distinguishing markers specific to MSC was carried out as follows.

Firstly, before the selection of the distinguishing markers specific to MSC, preprocess was carried out referring to flag information obtained from the analysis result of GeneChip (registered trademark). More specifically, genes indicated with flag information indicating expression of gene, that is, flag information "present call" or "margenal call" were selected. This was done because a gene with a low expression level in MSC would not allow to be detected exactly and accurately even if the expression thereof was different from that of the other genes.

Then, from among the genes satisfying the preprocess conditions, the distinguishing markers specific to MSC were selected. More specifically, this experiment examined and compared the expressions of various genes in the 5 types of cells: MSC, OS (obtained from the bone differentiation from MSC), CH (obtained from the cartilage differentiation from MSC), AD (obtained from the adipose differentiation from MSC), and FB. In this way, five relative expression intensities in the 5 types of cells were obtained per gene. One of the criterions for the selection was whether a difference between the expression level in MSC and a lowest one of the expression levels of the four cells other than MSC was 2 or more.

In other words, the one of the criterions selected genes whose expression level in MSC was double or greater than that in AD, that in CH, that in FB, and that in OS. This is because the difference being at least double makes it possible to distinguish MSC from other cells exactly and accurately. That is, a gene whose expression level in MSC is double or greater than those in the other cells can be used as the marker practically.

The thus calculated difference between the expression in MSC and those in the other cells can be an indicator to concretely express how intensely the expression of a gene is expressed in MSC than in the other cells. Thus, "the difference of 2 or greater" was set as one of the criterion for the selection. That is, one purpose of the present invention is to find a distinguishing marker for selecting undifferentiated mesenchymal stem cells specifically. Thus, the marker should be expressed at a remarkably greater expression level in mesenchymal stem cells than in the other cells. Because of this, the criterion for the selection was set as such.

Another criterion was "the expression level of the gene in MSC is high". This is because a small absolute value of the expression level in mesenchymal stem cells would make it difficult to detect the gene exactly and accurately or would lead to large errors. That is, it was considered that the candidates of the distinguishing markers should have a large absolute expression level. Thus, the another criterion was set, which is "the gene has an expression level of 0.5 or greater in MSC".

One hundred thirty nine genes, which satisfied the criterions, were selected as the distinguishing markers of undifferentiated MSC. Tables 3a to 3e show the 139 distinguishing markers and the evaluation thereof on the criterions in the selection.

TABLE 3a

|  | Gene symbol | Genbank number | Fold Average | Expression level |
|---|---|---|---|---|
| Classification 1 | | | | |
| ATP/GTP binding-1 | BRIP1 | NM_032043 | 4.7 | 0.2 |
| ATP/GTP binding-2 | PASK | NM_015148 | 9.4 | 0.3 |
| ATP/GTP binding-3 | RAC2 | NM_002872 | 13.6 | 1.0 |
| ATP/GTP binding-4 | KIF18A | NM_031217 | 4.8 | 0.4 |
| ATP/GTP binding-5 | NEK7 | NM_133494 | 2.9 | 34.2 |
| ATP/GTP binding-6 | ARL4C | NM_005737 | 3.7 | 8.6 |
| ATP/GTP binding-7 | EDEM1 | NM_014674 | 2.6 | 1.9 |
| ATP/GTP binding-8 | CAMK2D | NM_172127 | 2.7 | 4.2 |
| Classification 2 | | | | |
| binding-1 | PDE5A | NM_001083 | 7.0 | 0.8 |
| binding-2 | RGS4 | NM_005613 | 25.8 | 9.7 |
| binding-3 | EGFL3 | NM_001409 | 7.1 | 0.7 |
| binding-4 | FHL2 | NM_001450 | 4.4 | 41.6 |
| binding-5 | HRB2 | NM_007043 | 4.4 | 7.6 |
| binding-6 | CAPZA1 | NM_006135 | 2.3 | 30.9 |
| binding-7 | PAPPA2 | NM_020318 | 4.8 | 0.3 |
| binding-8 | LOXL2 | NM_002318 | 10.8 | 4.0 |
| binding-9 | LOX | NM_002317 | 4.7 | 9.7 |
| binding-10 | ADAMTS5 | NM_007038 | 3.4 | 5.6 |
| Classification 3 | | | | |
| cell growth and/or maintenance-1 | CCND1 | NM_053056 | 6.1 | 19.2 |
| cell growth and/or maintenance-2 | CDC25A | NM_001789 | 4.7 | 0.1 |
| cell growth and/or maintenance-3 | IER3 | NM_052815 | 6.8 | 8.5 |
| cell growth and/or maintenance-4 | BCL2 | NM_000633 | 5.0 | 0.3 |
| cell growth and/or maintenance-5 | NALP1 | NM_033004 | 6.3 | 5.6 |
| cell growth and/or maintenance-6 | PAK3 | NM_002578 | 12.8 | 0.3 |
| cell growth and/or maintenance-7 | PODXL | NM_001018111 | 6.8 | 0.7 |
| cell growth and/or maintenance-8 | CCL26 | NM_006072 | 7.7 | 0.4 |
| cell growth and/or maintenance-9 | FBLN1 | NM_006486 | 0.4 | 4.2 |

TABLE 3a-continued

| | Gene symbol | Genbank number | Fold Average | Expression level |
|---|---|---|---|---|
| cell growth and/or maintenance-10 | LAMA1 | NM_005559 | 4.5 | 0.8 |
| cell growth and/or maintenance-11 | NTNG1 | NM_014917 | 5.0 | 0.1 |

TABLE 3b

| | Gene symbol | Genbank number | Fold Average | Expression level |
|---|---|---|---|---|
| Classification 4 | | | | |
| cytokine-1 | GDF15 | NM_004864 | 4.4 | 3.0 |
| cytokine-2 | IL6 | NM_000600 | 14.9 | 3.9 |
| cytokine-3 | CTGF | NM_001901 | 5.6 | 60.6 |
| cytokine-4 | VEGF | NM_001025366 | 4.5 | 24.4 |
| cytokine-5 | VEGFC | NM_005429 | 4.1 | 9.8 |
| cytokine-6 | HGF | NM_000601 | 6.5 | 0.7 |
| Classification 5 | | | | |
| cytoskeleton-1 | KRT19 | NM_002276 | 130.0 | 1.7 |
| cytoskeleton-2 | KRTAP1-5 | NM_031957 | 29.8 | 14.5 |
| cytoskeleton-3 | KRTAP2-1 | BC012486 | 9.5 | 1.8 |
| cytoskeleton-4 | KRTHA4 | NM_021013 | 20.8 | 1.1 |
| cytoskeleton-5 | CKAP2 | NM_018204 | 4.8 | 0.1 |
| cytoskeleton-6 | KRTAP1-1 | NM_030967 | 38.1 | 2.5 |
| cytoskeleton-7 | KRT18 | NM_000224 | 30.2 | 2.1 |
| cytoskeleton-8 | KAP2.1B | AJ406929 | 18.7 | 0.3 |
| cytoskeleton-9 | SSH1 | NM_018984 | 3.0 | 6.7 |
| Classification 6 | | | | |
| enzyme 1 | LXN | NM_020169 | 10.1 | 7.6 |
| enzyme 2 | IFI30 | NM_006332 | 11.0 | 5.5 |
| enzyme 3 | CPA4 | NM_016352 | 8.1 | 1.0 |
| Classification 7 | | | | |
| extracellular matrix-1 | CHI3L1 | NM_001276 | 158.5 | 25.7 |
| extracellular matrix-2 | KRT23 | NM_015515 | 4.0 | 0.1 |
| extracellular matrix-3 | FLG | NM_002016 | 284.4 | 8.8 |
| extracellular matrix-4 | ADAMTS1 | NM_006988 | 7.2 | 6.9 |
| extracellular matrix-5 | FRMD5 | NM_001031729 | 23.8 | 2.1 |

TABLE 3c

| | Gene symbol | Genbank number | Fold Average | Expression level |
|---|---|---|---|---|
| Classification 8 | | | | |
| growth factor or receptor-1 | IGFBP1 | NM_000596 | 5.8 | 0.3 |
| growth factor or receptor-2 | CFI | NM_000204 | 28.7 | 1.7 |
| growth factor or receptor-3 | ESM1 | NM_007036 | 11.4 | 0.7 |
| growth factor or receptor-4 | F2RL1 | NM_005242 | 4.1 | 0.4 |
| growth factor or receptor-5 | MET | NM_000245 | 7.3 | 1.1 |
| growth factor or receptor-6 | HTR7 | NM_000872 | 3.7 | 0.2 |
| growth factor or receptor-7 | IGFBP3 | NM_001013398 | 3.4 | 90.7 |
| Classification 9 | | | | |
| membrane-1 | ABHD2 | NM_007011 | 4.5 | 2.1 |
| membrane-2 | ITGA2 | NM_002203 | 7.7 | 2.2 |
| membrane-3 | LAMA3 | NM_198129 | 6.6 | 1.3 |
| membrane-4 | NETO2 | NM_018092 | 7.9 | 4.9 |
| membrane-5 | NTN4 | NM_021229 | 5.5 | 6.5 |
| membrane-6 | PTGER1 | NM_000955 | 5.2 | 0.5 |
| membrane-7 | EPHB2 | NM_017449 | 12.4 | 0.4 |

TABLE 3c-continued

| | Gene symbol | Genbank number | Fold Average | Expression level |
|---|---|---|---|---|
| membrane-8 | SFRP1 | NM_003012 | 0.4 | 0.6 |
| membrane-9 | CD33L3 | NM_213602 | 11.9 | 1.3 |
| membrane-10 | GLIPR1 | NM_006851 | 4.8 | 6.8 |
| membrane-11 | UGCG | NM_003358 | 4.2 | 14.2 |
| membrane-12 | ADORA1 | NM_000674 | 3.5 | 0.5 |

TABLE 3d

| | Gene symbol | Genbank number | Fold Average | Expression level |
|---|---|---|---|---|
| Classification 10 | | | | |
| membrane binding protein-1 | ANXA10 | NM_007193 | 24.5 | 1.2 |
| membrane binding protein-2 | RARRES1 | NM_206963 | 7.2 | 0.5 |
| membrane binding protein-3 | HNT | NM_016522 | 13.1 | 16.0 |
| membrane binding protein-4 | CNTNAP3 | NM_033655 | 22.3 | 1.2 |
| Classification 11 | | | | |
| protein binding-1 | SYT1 | NM_005639 | 6.5 | 0.1 |
| protein binding-2 | MLF1 | NM_022443 | 4.6 | 0.1 |
| protein binding-3 | CDCP1 | NM_022842 | 17.4 | 0.9 |
| protein binding-4 | KIAA0746 | NM_015187 | 6.1 | 4.2 |
| protein binding-5 | PSCDBP | NM_004288 | 4.1 | 0.2 |
| protein binding-6 | SKI | NM_003036 | 3.0 | 2.8 |
| protein binding-7 | SNX25 | NM_031953 | 2.9 | 3.1 |
| protein binding-8 | CDH6 | NM_004932 | 4.5 | 0.7 |
| protein binding-9 | DCBLD2 | NM_080927 | 10.4 | 3.9 |
| protein binding-10 | ENG | NM_000118 | 3.2 | 8.7 |

TABLE 3d-continued

| Gene symbol | Genbank number | Fold Average | Expression level |
|---|---|---|---|
| Classification 12 | | | |
| protein modification-1 SH3RF1 | NM_020870 | 3.4 | 4.9 |
| protein modification-2 SMURF2 | NM_022739 | 5.0 | 19.7 |
| protein modification-3 TFPI2 | NM_006528 | 5.8 | 11.5 |
| protein modification-4 ITGB3 | NM_000212 | 8.1 | 0.3 |
| protein modification-5 MYPN | NM_032S78 | 4.8 | 0.3 |
| protein modification-6 LRP2BP | NM_018409 | 5.6 | 4.8 |
| protein modification-7 HECW2 | NM_020760 | 5.2 | 3.1 |
| protein modification-8 PKIA | NM_006823 | 4.3 | 0.5 |
| Classification 13 | | | |
| signal molecule-1 LYPD1 | NM_144586 | 29.6 | 0.9 |
| signal molecule-2 GATA6 | NM_005257 | 27.8 | 3.2 |
| signal molecule-3 RAB27B | NM_004163 | 10.1 | 0.8 |
| signal molecule-4 SOX11 | NM_003108 | 23.6 | 0.2 |
| signal molecule-5 ARHGAP22 | NM_021226 | 9.1 | 3.3 |

TABLE 3e

| Gene symbol | Genbank number | Fold Average | Expression level |
|---|---|---|---|
| Classification 14 | | | |
| transcription-1 ETV1 | NM_004956 | 6.9 | 3.6 |
| transcription-2 ETV5 | NM_004454 | 3.4 | 2.1 |
| transcription-3 FOXP1 | NM_032682 | 3.5 | 8.6 |
| transcription-4 HMGA2 | NM_003483 | 6.2 | 4.4 |
| transcription-5 KLF12 | NM_007249 | 5.2 | 0.4 |
| transcription-6 PRDM16 | NM_022114 | 8.1 | 0.7 |
| transcription-7 SIM2 | NM_009586 | 3.8 | 0.4 |
| transcription-8 SUHW2 | NM_080764 | 4.6 | 0.1 |
| transcription-9 ENO1 | NM_001428 | 3.7 | 0.3 |
| transcription-10 MITF | NM_198159 | 0.7 | 0.6 |
| transcription-11 TCF3 | NM_003200 | 3.2 | 0.2 |
| transcription-12 SMYD3 | NM_022743 | 3.0 | 7.5 |
| Classification 15 | | | |
| transport-1 ATP6V1G3 | NM_133262 | 3.9 | 0.3 |
| transport-2 KCTD16 | NM_020768 | 5.8 | 0.4 |
| transport-3 NUPL1 | NM_014089 | 4.0 | 0.9 |
| transport-4 SLC14A1 | NM_015865 | 22.3 | 6.5 |
| transport-5 SLC16A4 | NM_004696 | 5.6 | 5.1 |
| transport-6 SLC4A4 | NM_003759 | 6.6 | 0.4 |
| transport-7 SLC9A7 | NM_032591 | 7.3 | 0.6 |
| transport-8 TRPC4 | NM_016179 | 27.0 | 0.3 |
| transport-9 MCFD2 | NM_139279 | 3.7 | 10.0 |
| transport-10 SLC26A4 | NM_000441 | 4.1 | 0.3 |
| transport-11 MCOLN3 | NM_018298 | 3.1 | 0.6 |
| transport-12 SLC25A37 | NM_016612 | 2.2 | 4.2 |
| transport-13 SLC30A7 | NM_133496 | 2.7 | 3.5 |
| Classification 16 | | | |
| others-1 FLJ38725 | NM_153218 | 7.7 | 1.8 |
| others-2 KIAA1913 | NM_052913 | 7.2 | 20.2 |
| others-3 PHLDB2 | NM_145753 | 4.3 | 0.7 |
| others-4 PLCXD2 | NM_153268 | 7.2 | 0.3 |
| others-5 SAMD3 | NM_001017373 | 5.3 | 0.6 |
| others-6 ZNF423 | NM_015069 | 10.9 | 7.1 |
| others-7 FLJ33996 | NM_175894.2 | 13.6 | 0.2 |
| others-8 PLEKHK1 | NM_145307 | 5.0 | 0.1 |
| others-9 PTOV1 | NM_017432 | 3.2 | 0.0 |
| others-10 FAM40B | NM_020704 | 5.4 | 0.4 |
| others-11 ABI3BP | NM_015429 | 4.7 | 21.0 |
| others-12 NHS | NM_198270 | 4.4 | 0.4 |
| others-13 DTL | NM_016448 | 4.1 | 0.8 |
| others-14 C1GALT1 | NM_020156 | 3.8 | 2.9 |
| others-15 CPNE8 | NM_153634 | 3.1 | 1.0 |
| others-16 TMEM49 | NM_030938 | 1.2 | 10.1 |

In Tables 3a to 3e, the "Classification", "Gene symbol", "Genbank number" are same as in Tables 1a to 1j. The "Fold Average" indicates how high the expression of the gene was in comparison with the other cells. That is, the "Fold Average" is one of the criterions. In the present invention, a gene having "Fold Average" of 2 or more was judged as being preferable.

Moreover, the "Expression level" indicates how high the expression level was in MSC. This "Expression level" is one of the criterions. In the present invention, a gene having "Expression level" of 0.5 or more was judged as being preferable.

The "Fold Average" was calculated as follows. In the present Example, the relative expression levels in the 5 kinds of cells were obtained per gene. The expression level in MSC was compared with the other 4 expression levels. The "Fold Change" was a division of the expression level in MSC over another expression level. An average of the Fold changes of the cells was the "Fold Average". For example, if the expression level in MSC is 4.2, the expression level is OS is 0.3, the expression level in CH is 0.4, the expression level in AD is 1.5, and the expression level in FB is 1.3, then the "Fold Change" is MSC/OS=14.0. The fold changes of each cells were obtained in the same manner and the average of the fold changes was calculated as "Fold Average".

The 139 genes listed in Tables 3a to 3d, which met the criterions, can be used as the distinguishing marker of the present invention. Those one of the genes which met the two criterions are especially preferable.

Therefore, the expression of each of these genes in MSC is different from the expression thereof in the other connective tissue cells (FB, OS, CH, AD). That is, the genes are expressed specifically only in MSC but so weekly in the other connective tissue cells that the other connective tissue cells can be distinguished from MSC. Thus, the use of the gene expression as the distinguishing marker makes it possible to distinguish MSC solely and specifically.

INDUSTRIAL APPLICABILITY

As described above, undifferentiated mesenchymal stem cells can be differentiated to bone, cartilages, fats, muscles, tendons/ligaments, nerves, etc. Undifferentiated mesenchymal stem are expected as transplantation cells for remedying impairment of these tissues in regenerative medicine. To be applied to regenerative medicine, it is necessary to exactly, accurately and easily check that the cells are mesenchymal stem cells and that the mesenchymal stem cells are pluripotential. The present invention is a technical solution to this technical problem, and thus can make a great contribution to practical application of the regenerative medicine. The present invention is not only academically remarkable but also applicable to a wide range of industries including health industries, pharmaceutical industries, and the like.

The invention claimed is:

1. A method of separating mesenchymal stem cells from a sample, wherein the sample comprises mesenchymal stem cells collected from a living tissue and at least one additional cell collected from the living tissue and selected from the group consisting of fibroblasts, osteoblasts, chondrocytes, and adipocytes, the method comprising:
    distinguishing the mesenchymal stem cells from the at least one additional cell collected from the living tissue in the sample based on an expression profile of at least one distinguishing marker expressed in the mesenchymal stem cells; and
    separating the mesenchymal stem cells from the at least one additional cell collected from the living tissue based on the expression profile of the at least one distinguishing marker expressed in the mesenchymal stem cells;
wherein the at least one distinguishing marker includes at least one gene selected from the group consisting of latexin (LXN), interferon gamma-inducible protein 30 (IFI30), carboxypeptidase A4 (CPA4), chitinase 3-like 1 (CHI3L1), keratin 23 (KRT23), filaggrin (FLG), a disintegrin-like and metalloprotease with thrombospondin type 1 motif 1 (ADAMTS1), FERM domain containing 5 (FRMD5), insulin-like growth factor binding protein 1 (IGFBP1), complement factor I (CFI), endothelial cell-specific molecule 1 (ESM1), coagulation factor II receptor-like 1 (F2RL1), met proto-oncogene (MET), 5-hydroxytryptamine receptor 7 (HTR7), insulin-like growth factor binding protein 3 (IGFBP3), annexin A10 (ANXA10), retinoic acid receptor responder 1 (RARRES1), neurotrimin (HNT), contactin associated protein-like 3 (CNTNAP3), LY6/PLAUR domain containing 1 (LYPD1), GATA binding protein 6 (GATA6), RAB27B member RAS oncogene family (RAB27B), sex determining region Y-box 11 (SOX11), and Rho GTPase activating protein 22 (ARHGAP22).

2. The method as set forth in claim 1, wherein the at least one distinguishing marker comprises a combination of:
(a) at least one gene selected from the group consisting of LXN, IFI30, CPA4, CHI3L1, KRT23, FLG, ADAMTS1, FRMD5, IGFBP1, CFI, ESM1, F2RL1, MET, HTR7, IGFBP3, ANXA10, RARRES1, HNT, CNTNAP3, LYPD1, GATA6, RAB27B, SOX11, and ARHGAP22; and
(b) at least one gene selected from the group consisting of BRCA1 interacting protein C-terminal helicase 1 (BRIP1), PAS domain containing serine/threonine kinase (PASK), ras-related C3 botulinum toxin substrate 2 (RAC2), kinesin family member 18A (KIF18A), never in mitosis gene a-related kinase 7 (NEK7), ADP-ribosylation factor-like 4C (ARL4C), ER degradation enhancer mannosidase alpha-like 1 (EDEM1), calcium/calmodulin-dependent protein kinase II delta (CAMK2D), phosphodiesterase 5A cGMP-specific (PDE5A), regulator of G-protein signalling 4 (RGS4), EGF-like-domain multiple 3 (EGFL3), four and a half LIM domains 2 (FHL2), HIV-1 rev binding protein 2 (HRB2), capping protein muscle Z-line alpha 1 (CAPZA1), pappalysin 2 (PAPPA2), lysyl oxidase-like 2 (LOXL2), lysyl oxidase (LOX), ADAM metallopeptidase with thrombo-spondin type 1 motif 5 (ADAMTS5), cyclin D1 (CCND1), cell division cycle 25A (CDC25A), immediate early response 3 (IER3), B-cell CLL/lymphoma 2 (BCL2), NACHT leucine rich repeat and PYD containing 1 (NALP1), p21-activated kinase 3 (PAK3), podocalyxin-like (PODXL), chemokine ligand 26 (CCL26), fibulin 1 (FBLN1), laminin alpha 1 (LAMA1), netrin G1 (NTNG1), growth differentiation factor 15 (GDF15), interleukin 6 (IL6), connective tissue growth factor (CTGF), vascular endothelial growth factor (VEGF), vascular endothelial growth factor C (VEGFC), hepatocyte growth factor (HGF), keratin 19 (KRT19), keratin associated protein 1-5 (KRTAP1-5), keratin associated protein 2-1 (KRTAP2-1), keratin hair acidic 4 (KRTHA4), cytoskeleton associated protein 2 (CKAP2), keratin associated protein 1-1 (KRTAP1-1), keratin 18 (KRT18), keratin associated protein 2.1B (KAP2.1B), slingshot homolog 1 (SSH1), LXN, IFI30, CPA4, CHI3L1, KRT23, FLG, ADAMTS1, FRMD5, IGFBP1, CFI, ESM1, F2RL1, MET, HTR7, IGFBP3, abhydrolase domain containing 2 (ABHD2), integrin alpha 2 (ITGA2), laminin alpha 3 (LAMA3), neuropilin and tolloid-like 2 (NETO2), netrin 4 (NTN4), prostaglandin E receptor 1 subtype EP1 (PTGER1), EPH receptor B2 (EPHB2), secreted frizzled-related protein 1 (SFRP1), CD33 antigen-like 3 (CD33L3), GLI pathogenesis-related 1 (GLIPR1), UDP-glucose ceramide glucosyltransferase (UGCG), adenosine A1 receptor (ADORA1), ANXA10, RARRES1, HNT, CNTNAP3, synaptotagmin I (SYT1), myeloid leukemia factor 1 (MLF1), CUB domain-containing protein 1 (CDCP1), KIAA0746 protein (KIAA0746), pleckstrin homology-Sec7-coiled-coil domains-binding protein (PSCDBP), v-ski sarcoma viral oncogene homolog (SKI), sorting nexin 25 (SNX25), cadherin 6 type 2 K-cadherin (CDH6), discoidin-CUB-LCCL domain containing 2 (DCBLD2), endoglin (ENG), SH3 domain containing ring finger 1 (SH3RF1), SMAD specific E3 ubiquitin protein ligase 2 (SMURF2), tissue factor pathway inhibitor 2 (TFPI2), integrin beta 3 (ITGB3), myopalladin (MYPN), LRP2 binding protein (LRP2BP), HECT-C2-WW domain containing E3 ubiquitin protein ligase 2 (HECW2), protein kinase inhibitor alpha (PKIA), LYPD1, GATA6, RAB27B, SOX11, ARHGAP22, ets variant gene 1 (ETV1), ets variant gene 5 (ETV5), forkhead box P1 (FOXP1), high mobility group AT-hook 2 (HMGA2), Kruppel-like factor 12 (KLF12), PR domain containing 16 (PRDM16), single-minded homolog 2 (SIM2), suppressor of hairy wing homolog 2 (SUHW2), enolase 1 (ENO1), microphthalmia-associated transcription factor (MITF), transcription factor 3 (TCF3), SET and MYND domain containing 3 (SMYD3), ATPase-H+ transporting-lysosomal V1 subunit G isoform 3 (ATP6V1G3), potassium channel tetramerisation domain containing 16 (KCTD16), nucleoporin like 1 (NUPL1), solute carrier family 14 member 1 (SLC14A1), solute carrier family 16 member 4 (SLC16A4), solute carrier family 4 member 4 (SLC4A4), solute carrier family 9 isoform 7 (SLC9A7), transient receptor potential cation channel subfamily C member 4 (TRPC4), multiple coagulation factor deficiency 2 (MCFD2), solute carrier family 26 member 4 (SLC26A4), mucolipin 3 (MCOLN3), solute carrier family 25 member 37 (SLC25A37), solute carrier family 30 member 7 (SLC30A7), hypothetical protein FLJ38725 (FLJ38725), KIAA1913 (KIAA1913), pleckstrin homology-like domain family B member 2 (PHLDB2), phosphatidylinositol-specific phospholipase C X-domain containing 2 (PLCXD2), sterile alpha motif domain containing 3 (SAMD3), zinc finger protein 423 (ZNF423), hypothetical protein FLJ33996 (FLJ33996), pleckstrin homology domain containing family K member 1 (PLEKHK1), prostate tumor overexpressed gene 1 (PTOV1), family with sequence similarity 40 member B (FAM40B), ABI gene family member 3 binding protein (ABI3BP), Nance-Horan syndrome (NHS), denticleless homolog (DTL), core 1 synthase glycoprotein-N-acetylgalactosamine 3-beta-galactosyltransferase 1 (C1GALT1), copine VIII (CPNE8), and transmembrane protein 49 (TMEM49);
wherein the at least one (a) gene and the at least one (b) gene are not the same gene.

3. The method as set forth in claim 1, wherein the at least one distinguishing marker is selected from the group consisting of CHI3L1, FLG, CFI, ANXA10, LYPDC1, and GATA6.

4. The method as set forth in claim 3, wherein the at least one distinguishing marker is FLG.

5. The method as set forth in claim 4, wherein the at least one distinguishing marker further comprises at least one gene selected from the group consisting of TRPC4, ETV1, ETV5, FOXP1, GATA6, HMGA2, KLF12, PRDM16, SIM2, and SOX11.

6. The method as set forth in claim 4, wherein the at least one distinguishing marker further comprises one or more genes selected from the group consisting of BRIP1, PASK, RAC2, KIF18A, NEK7, ARL4C, EDEM1, CAMK2D, PDE5A, RGS4, EGFL3, FHL2, HRB2, CAPZA1, PAPPA2, LOXL2, LOX, ADAMTS5, CCND1, CDC25A, IER3, BCL2, NALP1, PAK3, PODXL, CCL26, FBLN1, LAMA1, NTNG1, GDF15, IL6, CTGF, VEGF, VEGFC, HGF, KRT19, KRTAP1-5, KRTAP2-1, KRTHA4, CKAP2, KRTAP1-1, KRT18, KAP2.1B, SSH1, LXN, IFI30, CPA4, CHI3L1, KRT23, FLG, ADAMTS1, FRMD5, IGFBP1, CFI, ESM1, F2RL1, MET, HTR7, IGFBP3, ABHD2, ITGA2, LAMA3, NETO2, NTN4, PTGER1, EPHB2, SFRP1, CD33L3, GLIPR1, UGCG, ADORA1, ANXA10, RARRES1, HNT, CNTNAP3, SYT1, MLF1, CDCP1, KIAA0746, PSCDBP, SKI, SNX25, CDH6, DCBLD2, ENG, SH3RF1, SMURF2, TFPI2, ITGB3, MYPN, LRP2BP, HECW2, PKIA, LYPD1, GATA6, RAB27B, SOX11, ARHGAP22, ETV1, ETV5, FOXP1, HMGA2, KLF12, PRDM16, SIM2, SUHW2, ENO1, MITF, TCF3, SMYD3, ATP6V1G3, KCTD16, NUPL1, SLC14A1, SLC16A4, SLC4A4, SLC9A7, TRPC4, MCFD, SLC26A4, MCOLN3, SLC25A37, SLC30A7, FLJ38725, KIAA1913, PHLDB2, PLCXD2, SAMD3, ZNF423, FLJ33996, PLEKHK1, PTOV1, FAM40B, ABI3BP, NHS, DTL, C1GALT1, CPNE8, and TMEM49.

7. A method of separating mesenchymal stem cells from a sample, wherein the sample comprises mesenchymal stem cells collected from a living tissue and at least one additional cell collected from the living tissue and selected from the group consisting of fibroblasts, osteoblasts, chondrocytes, and adipocytes, the method comprising:
  distinguishing the mesenchymal stem cells from the at least one additional cell collected from the living tissue in the sample based on an expression profile of a protein encoded by at least one distinguishing marker expressed in the mesenchymal stem cells; and
  separating the mesenchymal stem cells from the at least one additional cell collected from the living tissue based on the expression profile of the protein expressed in the mesenchymal stem cells;
  wherein the at least one distinguishing marker is selected from the group consisting of LXN, IFI30, CPA4, CHI3L1, KRT23, FLG, ADAMTS1, FRMD5, IGFBP1, CFI, ESM1, F2RL1, MET, HTR7, IGFBP3, ANXA10, RARRES1, HNT, CNTNAP3, LYPD1, GATA6, RAB27B, SOX11, and ARHGAP22.

\* \* \* \* \*